(12) United States Patent
Cecere et al.

(10) Patent No.: US 9,663,530 B2
(45) Date of Patent: May 30, 2017

(54) 5-OXA-2-AZABICYCLO[2.2.2]OCTAN-4-YL AND 5-OXA-2-AZABICYCLO[2.2.1]HEPTAN-4-YL DERIVATIVES

(71) Applicant: Hoffmann-La Roche Inc., Little Falls, NJ (US)

(72) Inventors: Giuseppe Cecere, Basel (CH); Guido Galley, Rheinfelden (DE); Yimin Hu, Shanghai (CN); Roger Norcross, Olsberg (CH); Philippe Pflieger, Schwoben (FR); Hong Shen, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/356,974

(22) Filed: Nov. 21, 2016

(65) Prior Publication Data
US 2017/0066775 A1    Mar. 9, 2017

Related U.S. Application Data

(63) Continuation of application No. PCT/EP2015/061348, filed on May 22, 2015.

(30) Foreign Application Priority Data

May 28, 2014 (WO) ................ PCT/CN2014/078644

(51) Int. Cl.
*C07D 491/08* (2006.01)
*A61K 31/537* (2006.01)

(52) U.S. Cl.
CPC ................................. *C07D 491/08* (2013.01)

(58) Field of Classification Search
None
See application file for complete search history.

(56) References Cited

FOREIGN PATENT DOCUMENTS

WO    2012/126922 A1    9/2012
WO    WO 2014072257 A1 *  5/2014   ........... C07D 413/12

OTHER PUBLICATIONS

Certified foreign priority document PCT/CN2014/078644 (May 28, 2014).*

* cited by examiner

*Primary Examiner* — Michael Barker

(57) ABSTRACT

The present invention relates to compounds of formula of formula I wherein X, Ar, $R^1$, m and n are as described herein, compositions containing compounds of formula I, methods of manufacture of compounds of formula I and methods of treating psychiatric disorders with compounds of formula I.

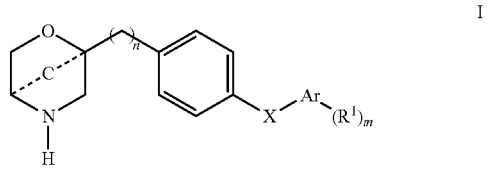

11 Claims, No Drawings

5-OXA-2-AZABICYCLO[2.2.2]OCTAN-4-YL AND 5-OXA-2-AZABICYCLO[2.2.1]HEPTAN-4-YL DERIVATIVES

CROSS REFERENCE TO RELATED APPLICATIONS

This application is a continuation of International Application No. PCT/EP2015/061348 having an international filing date of May 22, 2015 and which claims benefit under 35 U.S.C. §119 to International Application PCT/CN2014/078644 filed May 28, 2014. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Aberrant activity of Trace Amine Associated Receptors (TAARs), especially for TAAR1 is associated with psychiatric conditions such as depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well-known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison, and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the etiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

References used:
1 Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;
2 Wong, M. L. and Licinio, J. (2001) Research and treatment approaches to depression. *Nat. Rev. Neurosci.* 2, 343-351;
3 Carlsson, A. et al. (2001) Interactions between monoamines, glutamate, and GABA in schizophrenia: new evidence. *Annu. Rev. Pharmacol. Toxicol.* 41, 237-260;
4 Tuite, P. and Riss, J. (2003) Recent developments in the pharmacological treatment of Parkinson's disease. *Expert Opin. Investig. Drugs* 12, 1335-1352;
5 Castellanos, F. X. and Tannock, R. (2002) Neuroscience of attention-deficit/hyperactivity disorder: the search for endophenotypes. *Nat. Rev. Neurosci.* 3, 617-628;
6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychoparmacology*, San Juan, Puerto Rico] (1976);
7 Lindemann, L. and Hoener, M. (2005) A renaissance in trace amines inspired by a novel GPCR family. *Trends in Pharmacol. Sci.* 26, 274-281;
8 Branchek, T. A. and Blackburn, T. P. (2003) Trace amine receptors as targets for novel therapeutics: legend, myth and fact. *Curr. Opin. Pharmacol.* 3, 90-97;
9 Premont, R. T. et al. (2001) Following the trace of elusive amines. *Proc. Natl. Acad. Sci. U.S.A.* 98, 9474-9475;
10 Mousseau, D. D. and Butterworth, R. F. (1995) A high-affinity [3H] tryptamine binding site in human brain. *Prog. Brain Res.* 106, 285-291;
11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

BRIEF SUMMARY OF THE INVENTION

The invention relates to compounds of formula I

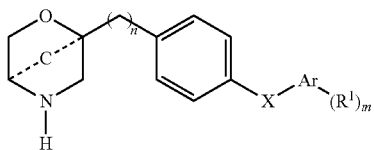

wherein
- - - - C - - - - - is —CH$_2$— or —CH$_2$—CH$_2$—;
X is —NH—, —C(O)NH— or —NHC(O)NH—;
Ar is phenyl or a 5 or 6-membered heteroaryl group containing one or two N atoms
R$^1$ is halogen, lower alkyl, lower alkyl substituted by halogen, lower alkoxy, lower alkoxy substituted by cycloalkyl, lower alkoxy substituted by halogen or is cycloalkyl;
-( )- is —CH$_2$—;
n is 0 or 1;
m is 0, 1 or 2;
or to a pharmaceutically suitable acid addition salt thereof, an enantiomer, a racemic mixture, a mixture of enantiomers or an optical isomer thereof.

In another embodiment, the present inventions provide for pharmaceutical compositions comprising compounds of Formula I.

In another embodiment, the present invention provides for methods of treating disease associated with trace amine associated receptors.

DETAILED DESCRIPTION OF THE INVENTION

There is a broad interest to increase the knowledge about trace amine associated receptors. Objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety, attention deficit hyperactivity disorder (ADHD) and diabetes.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

The term "halogen" denotes chlorine, iodine, fluorine and bromine. The preferred halogen group is fluorine.

As used herein, the term "lower alkyl substituted by halogen" denotes a saturated straight- or branched-chain group containing from 1 to 7 carbon atoms as defined for the term "lower alkyl", wherein at least one hydrogen atom is replaced by a halogen atom. A preferred halogen atom is fluoro. Examples of such groups are CF$_3$, CHF$_2$, CH$_2$F, CH$_2$CF$_3$ or CH$_2$CHF$_2$ The term "cycloalkyl" denotes a saturated carbon ring, containing from 3 to 6 carbon atoms, for example cyclopropyl, cyclobutyl, cyclopentyl or cyclohexyl.

The term "lower alkoxy substituted by halogen or substituted by cycloalkyl" denoted an alkoxy group as defined above, wherein at least one hydrogen atom is replaced by a halogen or by a cycloalkyl group, as defined above.

The term "5 or 6-membered heteroaryl group containing one or two N atoms" are selected from the group consisting of pyridinyl, pyrimidinyl, pyrazolyl or pyrazinyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

One embodiment of the invention are compounds of formula I, wherein ———C——— is —CH$_2$— and n is 1, for example the compounds:
1-(4-Chlorophenyl)-3-[4-[[(1S,4S)-5-oxa-2-azabicyclo [2.2.1]heptan-4-yl]methyl]phenyl]urea
1-(3-Chlorophenyl)-3-[4-[[(1S,4S)-5-oxa-2-azabicyclo [2.2.1]heptan-4-yl]methyl]phenyl]urea
1-[4-[[(1S,4S)-5-Oxa-2-azabicyclo[2.2.1]heptan-4-yl] methyl]phenyl]-3-[4-(trifluoromethyl)phenyl]urea
1-(2-Chlorophenyl)-3-[4-[[(1S,4S)-5-oxa-2-azabicyclo [2.2.1]heptan-4-yl]methyl]phenyl]urea
1-[4-[[(1S,4S)-5-Oxa-2-azabicyclo[2.2.1]heptan-4-yl] methyl]phenyl]-3-[3-(trifluoromethyl)phenyl]urea
4-Chloro-N-[4-[[(1S,4S)-5-oxa-2-azabicyclo[2.2.1]heptan-4-yl]methyl]phenyl]benzamide
4-Chloro-N-[4-[[(1S,4S)-5-oxa-2-azabicyclo[2.2.1]heptan-4-yl]methyl]phenyl]-3-propyl-1H-pyrazole-5-carboxamide
3-Chloro-N-[4-[[(1S,4S)-5-oxa-2-azabicyclo[2.2.1]heptan-4-yl]methyl]phenyl]benzamide
N-[4-[[(1S,4S)-5-Oxa-2-azabicyclo[2.2.1]heptan-4-yl] methyl]phenyl]-2-(trifluoromethyl)pyridine-4-carboxamide
4-Ethoxy-N-[4-[[(1S,4S)-5-oxa-2-azabicyclo[2.2.1]heptan-4-yl]methyl]phenyl]benzamide
1-[4-[[(1R,4R)-5-Oxa-2-azabicyclo[2.2.1]heptan-4-yl] methyl]phenyl]-3-[4-(trifluoromethyl)phenyl]urea 1-(4-Chlorophenyl)-3-[4-[[(1R,4R)-5-oxa-2-azabicyclo [2.2.1]heptan-4-yl]methyl]phenyl]urea
1-(3-Chlorophenyl)-3-[4-[[(1R,4R)-5-oxa-2-azabicyclo [2.2.1]heptan-4-yl]methyl]phenyl]urea
4-(Cyclopropylmethoxy)-N-[4-[[(1S,4S)-5-oxa-2-azabicyclo[2.2.1]heptan-4-yl]methyl]phenyl]benzamide
6-Ethoxy-N-[4-[[(1S,4S)-5-oxa-2-azabicyclo[2.2.1]heptan-4-yl]methyl]phenyl]pyridine-3-carboxamide
N-[4-[[(1S,4S)-5-Oxa-2-azabicyclo[2.2.1]heptan-4-yl] methyl]phenyl]-6-(2,2,2-trifluoroethoxy)pyridine-3-carboxamide
2-Cyclopropyl-N-[4-[[(1S,4S)-5-oxa-2-azabicyclo[2.2.1] heptan-4-yl]methyl]phenyl]pyrimidine-5-carboxamide
4-Chloro-3-cyclopropyl-N-[4-[[(1S,4S)-5-oxa-2-azabicyclo [2.2.1]heptan-4-yl]methyl]phenyl]-1H-pyrazole-5-carboxamide
5-Chloro-N-[4-[[(1S,4S)-5-oxa-2-azabicyclo[2.2.1]heptan-4-yl]methyl]phenyl]pyridin-2-amine
N-[4-[[(1S,4S)-5-Oxa-2-azabicyclo[2.2.1]heptan-4-yl] methyl]phenyl]-5-(trifluoromethyl)pyridin-2-amine
N-[4-[[(1S,4S)-5-Oxa-2-azabicyclo[2.2.1]heptan-4-yl] methyl]phenyl]-5-(trifluoromethyl)pyrazin-2-amine
N-[4-[[(1S,4S)-5-Oxa-2-azabicyclo[2.2.1]heptan-4-yl] methyl]phenyl]-5-(trifluoromethyl)pyrimidin-2-amine
3-Isopropyl-N-[4-[[(1S,4S)-5-oxa-2-azabicyclo[2.2.1]heptan-4-yl]methyl]phenyl]-1H-pyrazole-5-carboxamide
3-Chloro-N-[4-[[(1R,4R)-5-oxa-2-azabicyclo[2.2.1]heptan-4-yl]methyl]phenyl]benzamide
N-[4-[[(1R,4R)-5-Oxa-2-azabicyclo[2.2.1]heptan-4-yl] methyl]phenyl]-2-(trifluoromethyl)pyridine-4-carboxamide
4-Chloro-N-[4-[[(1R,4R)-5-oxa-2-azabicyclo[2.2.1]heptan-4-yl]methyl]phenyl]-3-propyl-1H-pyrazole-5-carboxamide
5-Chloro-N-[4-[[(1R,4R)-5-oxa-2-azabicyclo[2.2.1]heptan-4-yl]methyl]phenyl]pyridin-2-amine
1-(2-Chlorophenyl)-3-[4-[[(1R,4R)-5-oxa-2-azabicyclo [2.2.1]heptan-4-yl]methyl]phenyl]urea
1-[4-[[(1R,4R)-5-Oxa-2-azabicyclo[2.2.1]heptan-4-yl] methyl]phenyl]-3-[3-(trifluoromethyl)phenyl]urea
4-(Cyclopropylmethoxy)-N-[4-[[(1R,4R)-5-oxa-2-azabicyclo[2.2.1]heptan-4-yl]methyl]phenyl]benzamide
6-Ethoxy-N-[4-[[(1R,4R)-5-oxa-2-azabicyclo[2.2.1]heptan-4-yl]methyl]phenyl]pyridine-3-carboxamide
N-[4-[[(1R,4R)-5-Oxa-2-azabicyclo[2.2.1]heptan-4-yl] methyl]phenyl]-6-(2,2,2-trifluoroethoxy)pyridine-3-carboxamide
4-Chloro-3-cyclopropyl-N-[4-[[(1R,4R)-5-oxa-2-azabicyclo[2.2.1]heptan-4-yl]methyl]phenyl]-1H-pyrazole-5-carboxamide
4-Ethoxy-N-[4-[[(1R,4R)-5-oxa-2-azabicyclo[2.2.1]heptan-4-yl]methyl]phenyl]benzamide
2-Ethyl-N-[4-[[(1R,4R)-5-oxa-2-azabicyclo[2.2.1]heptan-4-yl]methyl]phenyl]pyrimidine-5-carboxamide
2-Cyclopropyl-N-[4-[[(1R,4R)-5-oxa-2-azabicyclo[2.2.1] heptan-4-yl]methyl]phenyl]pyrimidine-5-carboxamide
3-Isopropyl-N-[4-[[(1R,4R)-5-oxa-2-azabicyclo[2.2.1]heptan-4-yl]methyl]phenyl]-1H-pyrazole-5-carboxamide or
N-[4-[[(1R,4R)-5-Oxa-2-azabicyclo[2.2.1]heptan-4-yl] methyl]phenyl]-5-(trifluoromethyl)pyridin-2-amine.

One further embodiment of the invention are compounds of formula I, wherein ———C——— is —CH$_2$— and n is 0, for example the compounds:
5-Chloro-N-[4-[(1S,4R)-5-oxa-2-azabicyclo[2.2.1]heptan-4-yl]phenyl]pyridin-2-amine
5-Chloro-N-[4-[(1R,4S)-5-oxa-2-azabicyclo[2.2.1]heptan-4-yl]phenyl]pyridin-2-amine
4-Chloro-N-[4-[(1R,4S)-5-oxa-2-azabicyclo[2.2.1]heptan-4-yl]phenyl]benzamide
3-Chloro-N-[4-[(1R,4S)-5-oxa-2-azabicyclo[2.2.1]heptan-4-yl]phenyl]benzamide
N-[4-[(1R,4S)-5-Oxa-2-azabicyclo[2.2.1]heptan-4-yl]phenyl]-2-(trifluoromethyl)pyrimidin-4-amine
N-[4-[(1R,4S)-5-Oxa-2-azabicyclo[2.2.1]heptan-4-yl]phenyl]-2-(trifluoromethyl)pyridin-4-amine
4-Chloro-N-[4-[(1S,4R)-5-oxa-2-azabicyclo[2.2.1]heptan-4-yl]phenyl]benzamide
3-Chloro-N-[4-[(1S,4R)-5-oxa-2-azabicyclo[2.2.1]heptan-4-yl]phenyl]benzamide
N-[4-[(1S,4R)-5-Oxa-2-azabicyclo[2.2.1]heptan-4-yl]phenyl]-2-(trifluoromethyl)pyridine-4-carboxamide
N-[4-[(1S,4R)-5-Oxa-2-azabicyclo[2.2.1]heptan-4-yl]phenyl]-5-(trifluoromethyl)pyridin-2-amine or
N-[4-[(1S,4R)-5-Oxa-2-azabicyclo[2.2.1]heptan-4-yl]phenyl]-2-(trifluoromethyl)pyrimidin-4-amine.

One further embodiment of the invention are compounds of formula I, wherein ———C——— is —CH$_2$CH$_2$— and n is 1.

One further embodiment of the invention are compounds of formula I, wherein ———C——— is —CH$_2$CH$_2$— and n is 0 for example the compounds:
(RS)-5-Chloro-N-[4-(5-oxa-2-azabicyclo[2.2.2]octan-4-yl) phenyl]pyridin-2-amine
(RS)—N-[4-(5-Oxa-2-azabicyclo[2.2.2]octan-4-yl)phenyl]-5-(trifluoromethyl)pyridin-2-amine
(RS)-4-Chloro-N-[4-(5-oxa-2-azabicyclo[2.2.2]octan-4-yl) phenyl]benzamide
3-Chloro-N-[4-(5-oxa-2-azabicyclo[2.2.2]octan-4-yl)phenyl]benzamide
(RS)-4-(Cyclopropylmethoxy)-N-[4-(5-oxa-2-azabicyclo [2.2.2]octan-4-yl)phenyl]benzamide
(RS)-6-Ethoxy-N-[4-(5-oxa-2-azabicyclo[2.2.2]octan-4-yl) phenyl]pyridine-3-carboxamide
(RS)—N-[4-(5-Oxa-2-azabicyclo[2.2.2]octan-4-yl)phenyl]-6-(2,2,2-trifluoroethoxy)pyridine-3-carboxamide
(RS)-2-Cyclopropyl-N-[4-(5-oxa-2-azabicyclo[2.2.2]octan-4-yl)phenyl]pyrimidine-5-carboxamide
(RS)-4-Chloro-N-[4-(5-oxa-2-azabicyclo[2.2.2]octan-4-yl) phenyl]-3-propyl-1H-pyrazole-5-carboxamide
(RS)-2-Ethyl-N-[4-(5-oxa-2-azabicyclo[2.2.2]octan-4-yl) phenyl]pyrimidine-5-carboxamide
N-[4-(5-Oxa-2-azabicyclo[2.2.2]octan-4-yl)phenyl]-2-(trifluoromethyl)pyrimidin-4-amine
(RS)—N-[4-(5-Oxa-2-azabicyclo[2.2.2]octan-4-yl)phenyl]-2-(trifluoromethyl)pyridine-4-carboxamide
4-Ethoxy-N-[4-(5-oxa-2-azabicyclo[2.2.2]octan-4-yl)phenyl]benzamide
(RS)—N-[4-(5-Oxa-2-azabicyclo[2.2.2]octan-4-yl)phenyl]-5-(trifluoromethyl)pyrazin-2-amine
(RS)—N-[4-(5-Oxa-2-azabicyclo[2.2.2]octan-4-yl)phenyl]-5-(trifluoromethyl)pyrimidin-2-amine
(RS)-1-(4-Chlorophenyl)-3-[4-(5-oxa-2-azabicyclo[2.2.2] octan-4-yl)phenyl]urea
(RS)-1-[4-(5-Oxa-2-azabicyclo[2.2.2]octan-4-yl)phenyl]-3-[4-(trifluoromethyl)phenyl]urea or
(RS)-1-(3-Chlorophenyl)-3-[4-(5-oxa-2-azabicyclo[2.2.2] octan-4-yl)phenyl]urea.

The preparation of compounds of formula I of the present invention may be carried out in sequential or convergent synthetic routes. Syntheses of the compounds of the invention are shown in the following schemes 1 to 5 and in the description of 68 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 5, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods known in the art, for example, by processes described below, which process comprises a) cleaving off the N-protecting group ($R^2$) from compounds to a compound of formula I

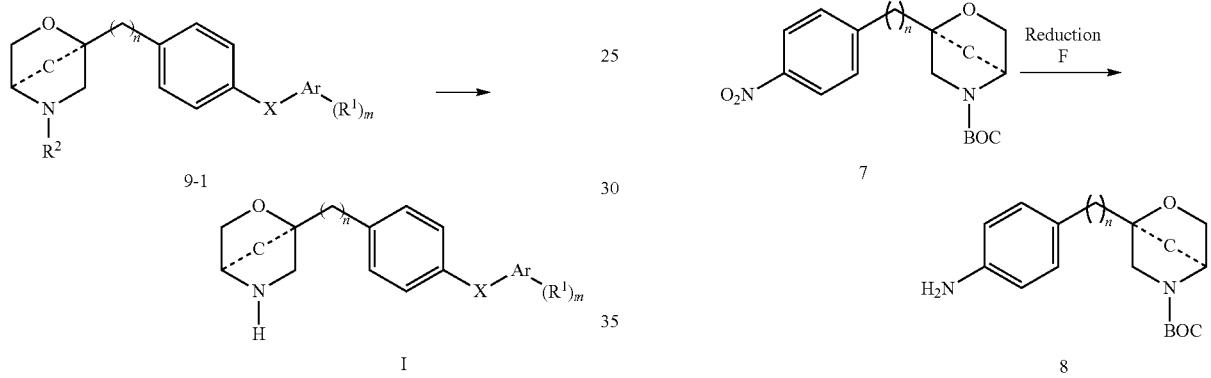

wherein $R^2$ is a N-protecting group selected from —C(O)O-tert-butyl or —C(O)CF$_3$ and the other definitions are as described above, and, optionally converting the compounds obtained into pharmaceutically acceptable acid addition salts.

GENERAL PROCEDURE

Scheme 1

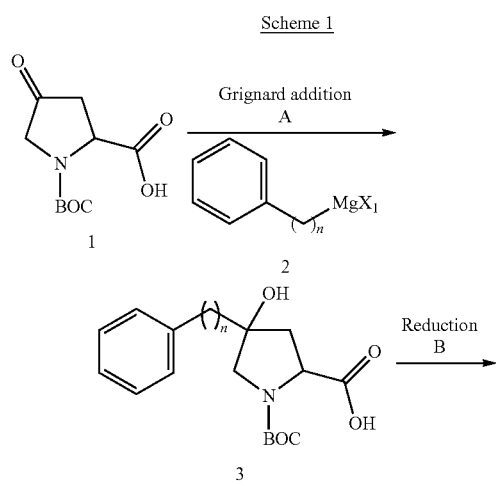

Step A: Grignard addition can be accomplished by the addition of phenyl or benzyl Grignard reagent 2 (n=0 or 1, $X_1$=Cl or Br) into a solution of N—BOC-4-oxo-proline 1 in anhydrous non-protic organic solvents such as THF and diethyl ether at a temperature between 0° C. and room temperature under an inert atmosphere.

Preferred conditions are using THF as solvent at 0° C. for 30 minutes to 3 hours.

Step B: Conversion of carboxylic acid 3 to the corresponding diol 4 can be accomplished by the reduction of the acid 3 with a borane reagent, such as borane dimethyl sulfide complex or borane-THF complex, in non-protic organic solvents such as THF, ethers, DME, and 1,4-dioxane, and TBME.

Preferred conditions are adding borane-THF complex into a solution of carboxylic acid 3 in THF at 0° C., and then continuing the reaction at reflux temperature for 3 hours.

Step C: Cyclisation can be accomplished by either a Mitsunobu-type reaction or a stepwise process involving sulphonate ester intermediates.

In the Mitsnobu-type reaction, diol 4 can be converted to protected bridged-morpholine 5 by treatment with triphenylphosphine and an azodicarboxylate, such as diethyl azodicarboxylate (DEAD) or diisopropyl azodicarboxylate (DIAD) in ethereal solvents such as diethyl ether, dioxane, THF, or TBME, or other non-protic organic solvents such as toluene and benzene. Preferred conditions are treating diol 4 with DIAD and triphenylphosphine at 0° C. and continuing the reaction at room temperature overnight.

In the stepwise process, the conversion can be accomplished by treatment of diol 4 with one equivalent of sulfonyl chloride, such as methanesulfonyl chloride or toluenesulfonyl chloride, in the presence of an organic base, such as pyridine, triethylamine, N,N-diisopropylethylamine or N-methylmorpholine, in ethereal solvents such as diethyl ether, dioxane, THF, or TBME, or using organic base as the solvent, at 0° C. to 50° C. The resulting sulphonate ester can be converted to protected bridged-morpholine 5 by treatment with a non-nucleophilic base such as sodium hydride, potassium tert-butoxide, or potassium 2-methyl-2-butoxide, in ethereal solvents such as diethyl ether, dioxane, THF, or TBME. Preferred conditions for the first step are adding toluenesulfonyl chloride into a solution of the diol 4 in pyridine at 0-5° C. and then allowing to react for 48 hours at 30° C. Preferred conditions for the second step are adding sodium hydride to a solution of sulphonate ester in THF at 0-5° C. and then allowing to react for 12 hours at room temperature.

Step D: Nitration can be accomplished by treatment of protected bridged-morpholine 5 in fuming nitric acid or in a mixture of nitric acid and other organic and inorganic acids such trifluoroacetic acid or sulfuric acid, at a temperature between −40° C. and room temperature, optionally in hydrocarbon or halogenated hydrocarbon solvents such as hexanes, dichloromethane, or 1,2-dichloroethane. Alternatively, the reaction can be performed by treatment of protected bridged-morpholine 5 with nitric acid salts, such as potassium nitrate, sodium nitrate or cesium nitrate, in other organic and inorganic acids such trifluoroacetic acid or sulfuric acid, at a temperature between −40° C. and room temperature.

Preferred conditions are treatment of protected bridged-morpholine 5 with potassium nitrate in trifluoroacetic acid at 0-5° C., and then allowing to react for 12 hours at room temperature.

Step E: During step E the nitrogen protecting group is removed under the nitration reaction conditions. Reprotection of the bridged-morpholine 6 can be accomplished by treatment with di-tert-butyl carbonate, optionally in the presence of an organic or inorganic base such as triethylamine, N,N-diisopropylethylamine, N-methylmorpholine, potassium carbonate, sodium carbonate, or cesium carbonate, in halogenated solvents such as dichloromethane or 1,2-dichloroethane or in ethereal solvents such as diethyl ether, dioxane, THF, or TBME. Preferred conditions are THF in the presence of potassium carbonate as the base at room temperature for 16 hours.

Step F: Reduction of the nitro group of 7 can be accomplished by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc, $CH_2Cl_2$, DMF or mixtures thereof.

Preferred conditions are using Pd—C as the catalyst and MeOH as the solvent and continuing the reaction under 50 psi $H_2$ at 30° C.

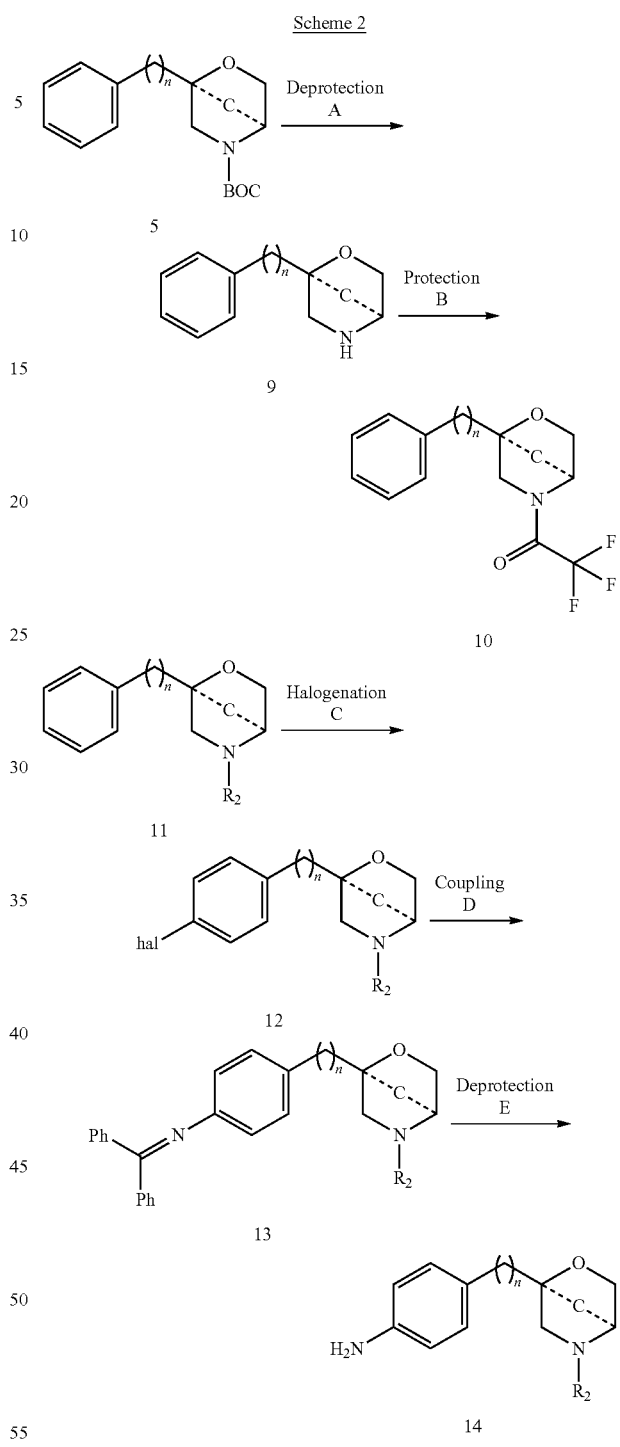

Step A: Deprotection of BOC-protected bridged-morpholine 5 can be accomplished by treatment with mineral acids such as $H_2SO_4$, $H_3PO_4$, $HNO_3$, or organic acids such as $CF_3COOH$, $CHCl_2COOH$, HOAc or p-toluenesulfonic acid in solvents such as $CH_2Cl_2$, $CHCl_3$, THF, dioxane, MeOH, EtOH, or $H_2O$ at a temperature between 0° C. and 80° C.

Preferred conditions are trifluroacetic acid with $CH_2Cl_2$ at 0° C.

Step B: Protection of bridged-morpholine 9 as trifluoroacetamides can be accomplished by treatment by trifluoroacetylating reagents such as trifluoroacetic anhydride, $CF_3CO_2Et$, $CF_3COO$-succinimidyl, (trifluoroacetyl)benzotriazole, $CF_3CO_2C_6F_5$, with bases such as triethylamine, diisopropylethylamine, pyridine, in solvents such as dichloromethane, THF, DMF, dioxane, MeOH, or EtOH at a temperature between 0° C. and 60° C.

Preferred conditions are trifluoroacetic anhydride with triethylamine as the base, in dichloromethane at 0° C. to 25° C.

Step C: Halogenation of bridged-morpholine 11 ($R_2$=BOC or $CF_3CO$) can be accomplished by treatment with halogenating reagents such as iodine, bromine, iodosuccinimide, bromosuccinimide, or polyvalent iodines together with iodine, such as [bis(trifluoroacetoxy)iodo]benzene/iodine and bis(acetoxy)phenyliodine/iodine, in halogenated solvents such as dichloromethane, chloroform, or tetrachloromethane, at a temperature between room temperature and 80° C.

Preferred conditions are bis(trifluoroacetoxy)iodo]benzene/iodine in tetrachloromethane at room temperature.

Step D: Coupling of aryl halide 12 ($R_2$=BOC or $CF_3CO$) with benzophenone imine can be accomplished in the presence of a palladium or copper catalyst, a ligand and a base in solvents such as dioxane, DME, THF, toluene and DMSO at elevated temperatures, for instance using a palladium-catalysed Buchwald-Hartwig reaction.

Preferred conditions are catalytic tris(dibenzylidineacetone)dipalladium(0), catalytic 4,5-bis(diphenylphosphino)-9,9-dimethylxanth (Xantphos), and $Cs_2CO_3$, in toluene at 100° C. for 5 hours.

Step E: Removal of the diphenylmethylene N-protecting group in 13 can be accomplished by hydrogenation with hydrogen under normal or elevated pressure or by transfer hydrogenation using ammonium formate or cyclohexadiene as hydrogen source in the presence of a catalyst such as $PtO_2$, Pd—C or Raney nickel in solvents such as MeOH, EtOH, $H_2O$, dioxane, THF, EtOAc, dichloromethane, chloroform, DMF or mixtures thereof.

The transformation can also be effected by treatment with hydroxylamine hydrochloride, together with a base such as sodium acetate, potassium acetate, sodium carbonate, potassium carbonate, cesium carbonate in solvents such as MeOH, EtOH, dioxane, THF, DMF or mixtures thereof.

Preferred conditions are hydroxylamine hydrochloride, together with sodium acetate, in MeOH at room temperature for 1 hour.

Scheme 3

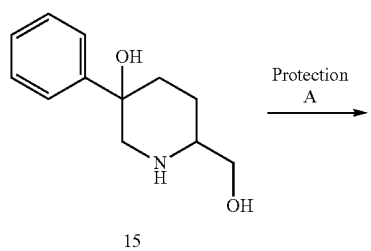

15

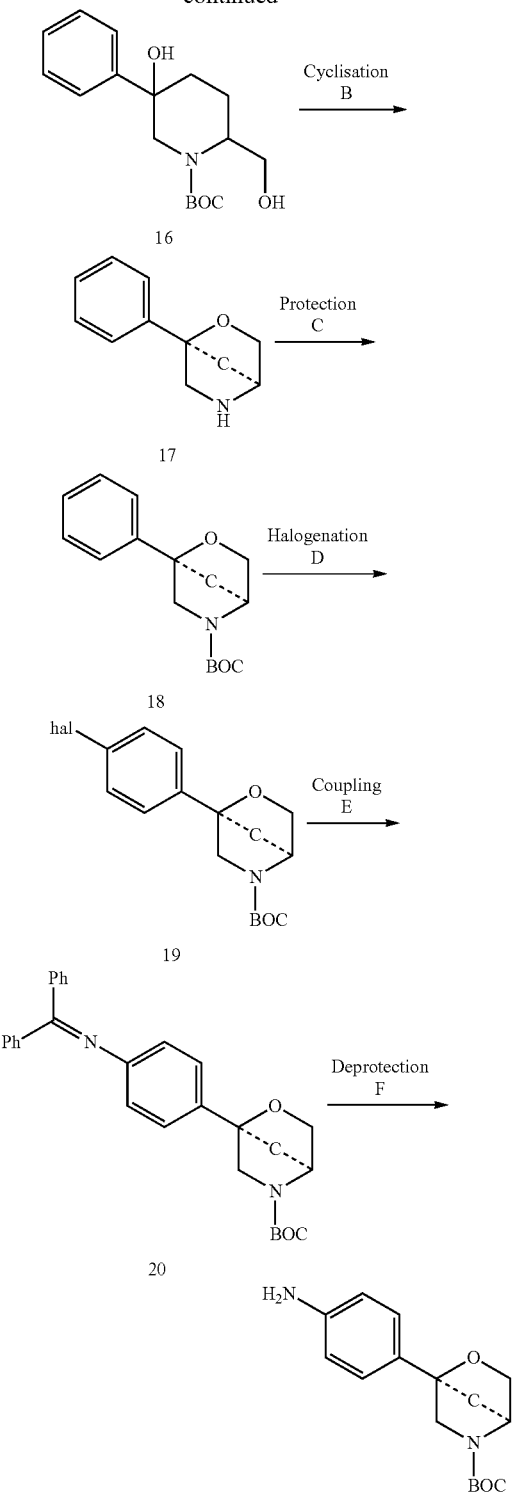

For ----C---- = —$CH_2CH_2$—

Diol 15 [CAS 282537-78-4] can be prepared according to literatured reported procedures (*Tetrahedron* 2000, 56, 3043-3051).

Step A: Selective protection of the nitrogen in diol 15 can be accomplished by treatment with di-tert-butyl carbonate, optionally in the presence of an organic base such as triethylamine, N,N-diisopropylamine or N-methylmorpholine, or an inorganic base such as sodium carbonate, potassium carbonate, cesium carbonate, in halogenated solvents such as dichloromethane or 1,2-dichloroethane or ethereal solvents such as diethyl ether, dioxane, THF or TBME. Preferred conditions are potassium carbonate as the base in THF as the solvent, at 60° C. for 1 hour.

Step B: Cyclisation of the diol 16 can be accomplished by treatment with a Lewis acid such as metal triflate salts, scandium(III) triflate for example, or boron trifluoride and its complexes including boron trifluoride diethyl etherate, boron trifluoride tetrahydrofuran complex, boron trifluoride dibutyl etherate, boron trifluoride acetonitrile complex. Optionally, $Et_3SiH$ can be used as an additive. Solvents can be dichloromethane, toluene, and hexanes.

Preferred conditions are boron trifluoride diethyl etherate as the Lewis acid, $Et_3SiH$ as the additive, in dichloromethane, at 0° C. to room temperature for 16 hours.

Step C: During step B the nitrogen protecting group is removed under the cyclisation reaction conditions. Reprotection of the nitrogen in 17 can be accomplished by treatment with di-tert-butyl carbonate, optionally in the presence of an organic base such as triethylamine, N,N-diisopropylamine or N-methylmorpholine, or an inorganic base such as sodium carbonate, potassium carbonate, cesium carbonate, in halogenated solvents such as dichloromethane or 1,2-dichloroethane or ethereal solvents such as diethyl ether, dioxane, THF or TBME.

Preferred conditions are potassium carbonate as the base in THF as the solvent, at 60° C. for 1 hour.

Step D: Halogenation of bridged-morpholine 18 can be accomplished by treatment with halogenating reagents such as iodine, bromine, iodosuccinimide, bromosuccinimide, or polyvalent iodines together with iodine, such as [bis(trifluoroacetoxy)iodo]benzene/iodine and bis(acetoxy)phenyliodine/iodine, in halogenated solvents such as dichloromethane, chloroform, or tetrachloromethane, at room temperature to 80° C.

Preferred conditions are bis(trifluoroacetoxy)iodo]benzene/iodine in tetrachloromethane at room temperature for 16 hours. $X_2$ is halogen.

Step E: Coupling of aryl halide 19 with benzophenone imine can be accomplished in the presence of a palladium or copper catalyst, a ligand and a base in solvents such as dioxane, DME, THF, toluene and DMSO at elevated temperatures, for instance using a palladium-catalysed Buchwald-Hartwig reaction.

Preferred conditions are catalytic tris(dibenzylidineacetone)dipalladium(0), catalytic 4,5-bis(diphenylphosphino)-9,9-dimethylxanth (Xantphos), and $Cs_2CO_3$, in dioxane at 90° C. for 16 hours.

Step F: Removal of the diphenylmethylene N-protecting group in 20 can be accomplished by hydrogenation with hydrogen under normal or elevated pressure or by transfer hydrogenation using ammonium formate or cyclohexadiene as hydrogen source in the presence of a catalyst such as $PtO_2$, Pd—C or Raney nickel in solvents such as MeOH, EtOH, $H_2O$, dioxane, THF, EtOAc, dichloromethane, chloroform, DMF or mixtures thereof.

The transformation can also be effected by treatment with hydroxylamine hydrochloride, together with a base such as sodium acetate, potassium acetate, sodium carbonate, potassium carbonate, cesium carbonate in solvents such as MeOH, EtOH, dioxane, THF, DMF or mixtures thereof.

Preferred conditions are hydroxylamine hydrochloride, together with sodium acetate, in MeOH at room temperature for 2 hours.

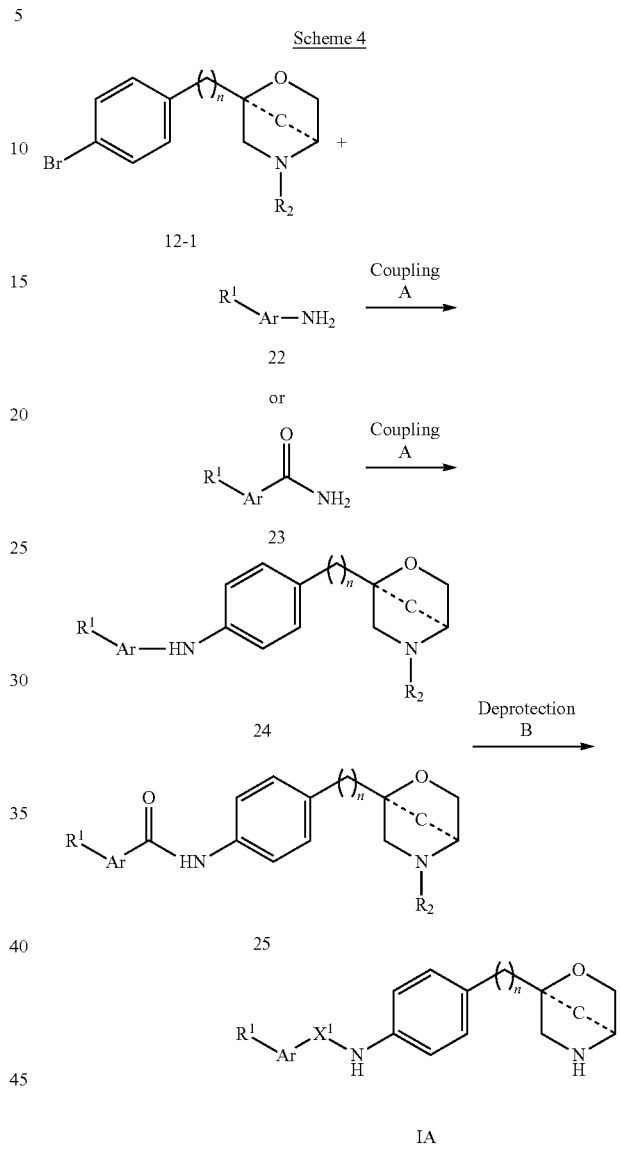

Scheme 4

$X^1$ is NH or —C(O)NH—

Step A: Coupling of aryl halide 12-1 ($R_2$=BOC or $CF_3CO$) with an aryl amine 22 or an aryl amide 23 can be accomplished by treatment with a palladium or copper catalyst, a ligand, and a base in solvents such as dioxane, DMF, THF, toluene, DMF and DMSO at elevated temperatures, for instance using a palladium-catalyzed Buchwald-Hartwig reaction.

Preferred conditions are catalytic tris(dibenzylidineacetone)dipalladium(0), catalytic 4,5-bis(diphenylphosphino)-9,9-dimethylxanth (Xantphos), and $Cs_2CO_3$, in dioxane at 90° C. for 16 hours.

Step B: Removal of BOC N-protecting group can be effected with mineral acids such as HCl, $H_2SO_4$, or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH, or $H_2O$ at 0-80° C.

Preferred conditions are $CF_3COOH$ as the acid in $CH_2Cl_2$ at room temperature for 2 hours.

Scheme 5

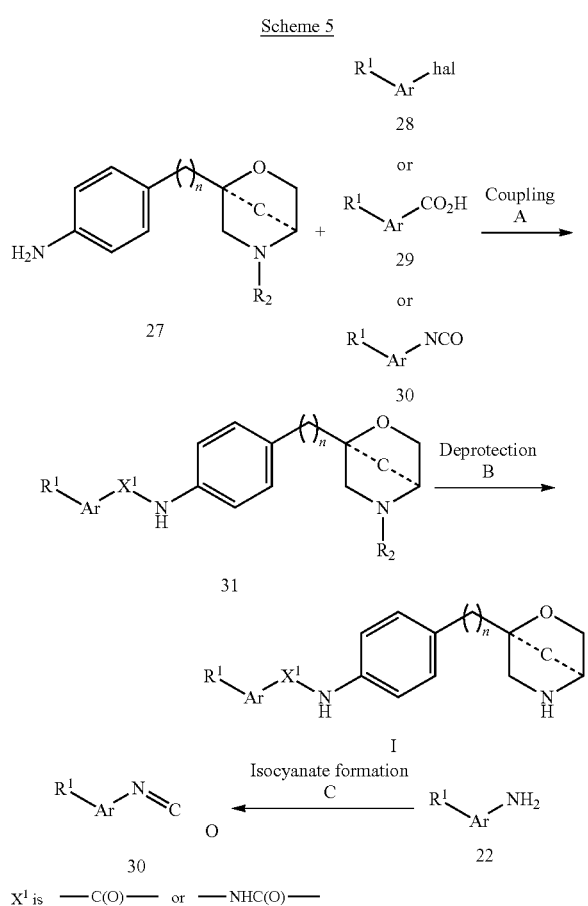

X¹ is —C(O)— or —NHC(O)—

Step A: Coupling of aniline 27 (R₂=BOC or CF₃CO) with an aryl halide 28 can be accomplished by treatment with a palladium or copper catalyst, a ligand, and a base in solvents such as dioxane, DMF, THF, toluene, DMF and DMSO at elevated temperatures, for instance using a palladium-catalyzed Buchwald-Hartwig reaction.

Preferred conditions are catalytic tris(dibenzylidineacetone)dipalladium(0), catalytic 4,5-Bis(diphenylphosphino)-9,9-dimethylxanth (Xantphos), and Cs₂CO₃, in dioxane at 90° C. for 12 hours.

Amide formation with aniline 27 (R₂=BOC or CF₃CO) and a carboxylic acid 29 can be accomplished by reaction in the presence of a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, dioxane, THF, DME, or TBME.

Preferred conditions are HATU with N,N-diisopropylethylamine in DMF at room temperature for 16 hours.

Urea formation with aniline 27 (R₂=BOC or CF₃CO) and an isocyanate 30 can be accomplished by reaction in the presence of an organic base such as triethylamine, N,N-diisopropylethylamine or N-methylmorpholine in halogenated solvents such as dichloromethane, 1,2-dichloroethane, chlorobenzene.

Preferred conditions are triethylamine as the base in dichloromethane at room temperature for 16 hours.

Step B: Removal of BOC N-protecting group can be effected with mineral acids such as HCl, H₂SO₄, or H₃PO₄ or organic acids such as CF₃COOH, CHCl₂COOH, HOAc or p-toluenesulfonic acid in solvents such as CH₂Cl₂, CHCl₃, THF, MeOH, EtOH, or H₂O at 0-80° C.

Preferred conditions are CF₃COOH as the acid in CH₂Cl₂ at room temperature for 2 hours.

Step C: If isocynate 30 is not commercially available, it can be prepared by treatment of corresponding amine 22 with triphosgene, diphosgene or phosgene in halogenated solvents such as dichloromethane or 1,2-dichloroethane in the presence of an organic base such as triethylamine or N,N-diisopropylethylamine or an inorganic base such as sodium carbonate or potassium carbonate.

Preferred conditions are triphosgene and sodium carbonate in a mixture of dichloromethane and water at room temperature for 2-3 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

EXAMPLE 1

1-(4-Chlorophenyl)-3-[4-[[(1S,4S)-5-oxa-2-azabicyclo[2.2.1]heptan-4-yl]methyl]phenyl]urea

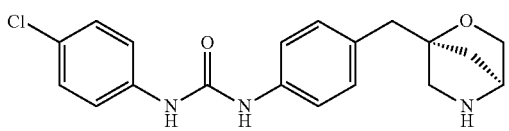 [SMILES: O=C(Nc1ccc(Cl)cc1)Nc1ccc(C[C@]23CN[C@H](CO2)C3)cc1]

a) (2S)-4-Benzyl-1-tert-butoxycarbonyl-4-hydroxypyrrolidine-2-carboxylic acid

To a solution of benzylmagnesium bromide (1 M in THF, 436 mL, 436 mmol, CAS: 1589-82-8) was added dropwise at 0° C. a solution of N-Boc-4-oxo-L-proline (25 g, 109 mmol, CAS: 84348-37-8) in THF (200 mL). The reaction mixture was stirred at 0° C. for 3 hours until TLC analysis indicated complete consumption of the starting material. To the reaction mixture was added saturated aqueous NH$_4$Cl solution (200 mL) at 0° C. The mixture was warmed to room temperature and extracted with ethyl acetate (2×300 mL). The combined organic layers were washed with brine (500 mL), dried over Na$_2$SO$_4$, and concentrated under reduced pressure. Purification by flash chromatography (silica gel, CH$_2$Cl$_2$/MeOH=100/1-20/1 by vol) gave (2S)-4-benzyl-1-tert-butoxycarbonyl-4-hydroxy-pyrrolidine-2-carboxylic acid (16 g, 46% yield) as a white solid. MS(ESI): 322.0 ([M+H]$^+$)

b) tert-Butyl (2 S)-4-benzyl-4-hydroxy-2-(hydroxymethyl)pyrrolidine-1-carboxylate To a solution of (2S)-4-benzyl-1-tert-butoxycarbonyl-4-hydroxy-pyrrolidine-2-carboxylic acid (64 g, 0.2 mol) in THF (300 mL) was added borane tetrahydrofuran complex (1 M in THF, 600 mL, 0.6 mol) at 0° C. The solution was refluxed for 4 hours until TLC analysis indicated complete consumption of the starting material. MeOH (500 mL) was added. The solution was stirred at room temperature for 2 hours. Volatiles were removed under reduced pressure. Purification by flash chromatography (silica gel, CH$_2$Cl$_2$/MeOH=100/1~20/1 by vol) gave tert-butyl (2S)-4-benzyl-4-hydroxy-2-(hydroxymethyl)pyrrolidine-1-carboxylate (33 g, 54% yield) as a white solid. MS(ESI): 308.0 ([M+H]$^+$).

c) tert-Butyl (1S,4S)-4-benzyl-5-oxa-2-azabicyclo[2.2.1]heptane-2-carboxylate To a solution of tert-butyl (2S)-4-benzyl-4-hydroxy-2-(hydroxymethyl)pyrrolidine-1-carboxylate (14 g, 45.5 mmol) in pyridine (160 mL) was added p-toluenesulfonyl chloride (11.3 g, 59.2 mmol, CAS: 98-59-9) at 0° C. The reaction mixture was stirred at 30° C. for 48 hours. The mixture was poured into 10% aqueous citric acid (1 L) and extracted with CH$_2$Cl$_2$ (1 L×2). The combined organic layers were washed with brine (1 L×5), dried over Na$_2$SO$_4$, and concentrated under reduced pressure. Purification by flash chromatography (silica gel, petroleum ether/ethyl acetate=30/1~10/1 by vol) gave tert-butyl (2S)-4-benzyl-4-hydroxy-2-(p-tolylsulfonyloxymethyl)pyrrolidine-1-carboxylate (10.1 g) as a white solid.

To a solution of tert-butyl (2S)-4-benzyl-4-hydroxy-2-(p-tolylsulfonyloxymethyl)pyrrolidine-1-carboxylate (10.1 g, 21.9 mmol) in THF (500 mL) at 0° C. was added NaH (1.31 g, 60%, 32.8 mmol). The reaction mixture was stirred at 25° C. overnight. Water (50 mL) was added. The mixture was extracted with CH$_2$Cl$_2$ (200 mL×2). The combined organic layers were washed with brine (100 mL), dried over Na$_2$SO$_4$, and concentrated under reduced pressure. Purification by flash chromatography (silica gel, petroleum ether/ethyl acetate=20/1~10/1 by vol) gave tert-butyl (1S,4S)-4-benzyl-5-oxa-2-azabicyclo[2.2.1]heptane-2-carboxylate (4.8 g, 36% yield over 2 steps) as a white solid. MS(ESI): 290.0 ([M+H]$^+$).

$^1$H NMR (CDCl$_3$, 400 MHz): δ 7.32-7.24 (m, 5H), 4.41 (d, 1H), 3.88 (dd, 1H), 3.82 (s, 1H), 3.26 (d, 2H), 3.11 (m, 2H), 1.73 (m, 1H), 1.59 (s, 1H), 1.44 (s, 9H).

d) (1S,4S)-4-[(4-Nitrophenyl)methyl]-5-oxa-2-azabicyclo[2.2.1]heptane

To a solution of tert-butyl (1S,4S)-4-benzyl-5-oxa-2-azabicyclo[2.2.1]heptane-2-carboxylate (4.8 g, 16.58 mmol) in TFA (70 mL, CAS: 76-05-1) was added KNO$_3$ (5.02 g, 49.8 mmol) at 0° C. The reaction mixture was stirred at room temperature overnight. Volatiles were removed under reduced pressure. Water (100 mL) was added. The pH was adjusted to 7~8 by addition of NaHCO$_3$. The mixture was extracted with CH$_2$Cl$_2$/MeOH (10/1 by vol, 200 mL×3). The combined organic layers were washed with brine (200 mL), dried over Na$_2$SO$_4$, and concentrated under reduced pressure to give crude (1S,4S)-4-[(4-nitrophenyl)methyl]-5-oxa-2-azabicyclo[2.2.1]heptane (3.88 g, 100% of yield) as a yellow oil. MS(ESI): 290.0 ([M+H]$^+$).

e) tert-Butyl (1S,4S)-4-[(4-nitrophenyl)methyl]-5-oxa-2-azabicyclo[2.2.1]heptane-2-carboxylate To a solution of crude (1S,4S)-4-[(4-nitrophenyl)methyl]-5-oxa-2-azabicyclo[2.2.1]heptane (3.88 g, 16.58 mmol, from step d) in a mixture of THF (50 mL) and H$_2$O (20 mL) were added Boc$_2$O (3.58 g, 16.58 mmol, CAS: 24424-99-5) and K$_2$CO$_3$ (4.58 g, 33.2 mmol). The reaction mixture was stirred at room temperature overnight. The mixture was diluted with ethyl acetate (100 mL), washed with brine (50 mL), dried over Na$_2$SO$_4$, and concentrated under reduced pressure. Purification by flash chromatography (silica gel, petroleum ether/ethyl acetate=30/1~10/1 by vol) gave tert-butyl (1S,4S)-4-[(4-nitrophenyl)methyl]-5-oxa-2-azabicyclo[2.2.1]heptane-2-carboxylate (2.8 g, 50% of yield over 2 steps) as a yellow oil. MS(ESI): 357.1 ([M+Na]$^+$), 279.1 ([M-C$_4$H$_8$+H]$^+$), 235.1 ([M-C$_4$H$_8$—CO$_2$+H]$^+$).

f) tert-Butyl (1S,4S)-4-[(4-aminophenyl)methyl]-5-oxa-2-azabicyclo[2.2.1]heptane-2-carboxylate To a solution of tert-butyl (1S,4S)-4-[(4-nitrophenyl)methyl]-5-oxa-2-azabicyclo[2.2.1]heptane-2-carboxylate (5.2 g, 15.5 mmol) in MeOH (200 mL) was added 10% Pd on carbon (wet, 5 g, CAS: 7440-05-3). The reaction mixture was stirred under 45 psi H$_2$ atmosphere at 30° C. overnight. The solution was filtered. The filtrate was concentrated under reduced pressure and dried further under high vacuum to give tert-butyl (1 S,4S)-4-[(4-aminophenyl)methyl]-5-oxa-2-azabicyclo[2.2.1]heptane-2-carboxylate (4.5 g, 96% yield) as a yellow oil.

$^1$H NMR (CDCl$_3$, 400 MHz): δ 7.01 (m, 2H), 6.63 (m, 2H), 4.40 (d, 1H), 3.88 (dd, 1H), 3.83 (s, 1H), 3.24 (d, 2H), 2.98 (m, 2H), 1.68 (m, 2H), 1.44 (s, 9H).

g) 1-(4-Chlorophenyl)-3-[4-[[(1S,4S)-5-oxa-2-azabicyclo[2.2.1]heptan-4-yl]methyl]phenyl]urea To a solution of tert-butyl (1S,4S)-4-[(4-aminophenyl)methyl]-5-oxa-2-azabicyclo[2.2.1]heptane-2-carboxylate (50 mg, 0.16 mmol) and Et$_3$N (25 mg, CAS: 121-44-8) in CH$_2$Cl$_2$ (1 mL) was added 4-chlorophenyl isocyanate (30 mg CAS: 104-12-1) at room temperature. The reaction mixture was stirred overnight. The reaction mixture was diluted with CH$_2$Cl$_2$ (20 ml), washed with aqueous NaHCO$_3$ solution (5 ml), dried over Na$_2$SO$_4$, and concentrated under reduced pressure. The mixture was dissolved in CH$_2$Cl$_2$ (2 mL). TFA (0.5 ml, CAS: 76-05-1) was added. The reaction mixture was stirred at room temperature for an hour. Volatiles were removed under reduced pressure. The crude mixture was purified by Prep-HPLC (mobile phase A: H$_2$O, B: CH$_3$CN with 0.1% TFA, C18 column) to give 1-(4-chlorophenyl)-3-[4-[[(1S,4S)-5-oxa-2-azabicyclo[2.2.1]

heptan-4-yl]methyl]phenyl]urea (25 mg, 44% yield) as a white solid. MS (ESI): 360.1 ([{$^{37}$Cl}M+H]$^+$), 358.1 ([{$^{35}$Cl}M+H]$^+$).

$^1$H NMR (methanol-d$^4$, 400 MHz): δ 7.43 (d, 2H), 7.36 (d, 2H), 7.27 (d, 2H), 7.20 (d, 2H), 3.87 (m, 3H), 3.03 (m, 2H), 2.97 (m, 2H), 1.91 (s, 1H), 1.77 (s, 1H).

EXAMPLE 2

1-(3-Chlorophenyl)-3-[4-[[(1S,4S)-5-oxa-2-azabicyclo[2.2.1]heptan-4-yl]methyl]phenyl]urea

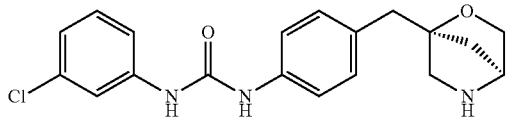 [SMILES: O=C(Nc1ccc(C[C@]23CN[C@H](CO2)C3)cc1)Nc1cccc(Cl)c1]

The title compound was obtained in analogy to example 1 using 3-chlorophenyl isocyanate (CAS: 2909-38-8) instead of 4-chlorophenyl isocyanate in step (g). White solid.

MS (ESI): 360.0 ([{$^{37}$Cl}M+H]$^+$), 358.0 ([{$^{35}$Cl}M+H]$^+$).

EXAMPLE 3

(RS)-5-Chloro-N-[4-(5-oxa-2-azabicyclo[2.2.2]octan-4-yl)phenyl]pyridin-2-amine

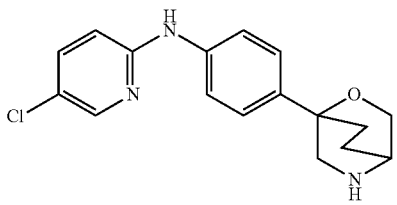 [SMILES: Clc1ccc(Nc2ccc(C34CCC(CO3)NC4)cc2)nc1]

a) tert-Butyl 5-hydroxy-2-(hydroxymethyl)-5-phenyl-piperidine-1-carboxylate 6-(Hydroxymethyl)-3-phenyl-piperidin-3-ol (mixture of (2R,5S)-rel-5-hydroxy-5-phenyl-2-piperidinemethanol [CAS: 282537-78-4] and (2R,5R)-rel-5-hydroxy-5-phenyl-2-piperidinemethanol [CAS: 282537-80-8]) was prepared according to a known literature procedure (X. Wu et al. I Tetrahedron 2000, 56, 3043-3051).

To a stirred solution of 6-(hydroxymethyl)-3-phenyl-piperidin-3-ol (31.0 g, 150 mmol) and Boc$_2$O (39.2 g, 179 mmol) in THF (500 mL) was added K$_2$CO$_3$ (62.0 g, 449 mmol) at room temperature. The reaction mixture was stirred at 60° C. for an hour. The mixture was cooled to room temperature and filtered. The filtrate was collected and concentrated under reduced pressure to give the crude product as an off-white solid. The crude product was purified by flash chromatography (silica gel, CH$_2$Cl$_2$/MeOH=50:1 to 10:1 by vol) to give tert-butyl 5-hydroxy-2-(hydroxymethyl)-5-phenyl-piperidine-1-carboxylate (26 g, 65% yield) at a white solid. MS (ESI): 308.1 ([M+H]$^+$).

b) 4-Phenyl-5-oxa-2-azabicyclo[2.2.2]octane

To a solution of tert-butyl 5-hydroxy-2-(hydroxymethyl)-5-phenyl-piperidine-1-carboxylate (307 mg, 1.0 mmol) and Et$_3$SiH (1.2 g, 10.0 mmol, CAS: 617-86-7) in CH$_2$Cl$_2$ (20 mL) at 0° C. was added boron trifluoride diethyl etherate (1.14 g, 8.0 mmol, CAS: 109-63-7). The reaction mixture was stirred at room temperature overnight. The mixture was quenched with saturated aqueous NaHCO$_3$. The mixture was extracted with CH$_2$Cl$_2$ (3×200 mL). The combined organic layers were washed with water and brine. Volatiles were removed under reduced pressure. The residue was dried further under high vacuum to give crude 4-phenyl-5-oxa-2-azabicyclo[2.2.2]octane (0.3 g) as a yellow oil. MS(ESI): 190.1 ([M+H]$^+$).

$^1$H NMR (methanol-d$^4$, 400 MHz): δ 7.49-7.32 (m, 5H), 4.42 (d, 1H), 4.21 (d, 1H), 3.75 (s, 1H), 3.68 (d, 1H), 3.49 (d, 1H), 2.36 (m, 2H), 2.20 (m, 2H).

c) tert-Butyl 4-phenyl-5-oxa-2-azabicyclo[2.2.2]octane-2-carboxylate

To a stirred solution of 4-phenyl-5-oxa-2-azabicyclo[2.2.2]octane (5.0 g, 26.4 mmol), Boc$_2$O (8.6 g, 39.6 mmol, CAS: 24424-99-5) in THF (200 mL) was added K$_2$CO$_3$ (11.0 g, 79.2 mmol) at room temperature. The reaction mixture was stirred at 60° C. for an hour until TLC analysis indicated the completion of the reaction. The mixture was filtered. The filtrate was concentrated under reduced pressure. Purification by flash chromatography (silica gel, petroleum ether: ethyl acetate=100:0 to 20:1 by vol) gave tert-butyl 4-phenyl-5-oxa-2-azabicyclo[2.2.2]octane-2-carboxylate (1.94 g, 25% yield over 2 steps) as a white solid. MS(ESI): 234.1 ([M-C$_4$H$_8$+H]$^+$), 190.1 ([M-C$_4$H$_8$—CO$_2$+H]$^+$).

d) tert-Butyl 4-(4-iodophenyl)-5-oxa-2-azabicyclo[2.2.2]octane-2-carboxylate

To a solution of tert-butyl 4-phenyl-5-oxa-2-azabicyclo[2.2.2]octane-2-carboxylate (289 mg, 1.0 mmol) in CCl$_4$ (3.3 mL) were added [bis(trifluoroacetoxy)iodo]benzene (516 mg, 1.2 mmol, CAS: 2712-78-9) and iodine (254 mg, 1.0 mmol, CAS: 7553-56-2). The reaction mixture was stirred at room temperature overnight until LCMS analysis indicated completion of the reaction. The mixture was diluted with CH$_2$Cl$_2$ (50 mL), washed with 5% NaHSO$_3$ (20 mL) and 10% NaCl (20 mL), and dried over MgSO$_4$. The mixture was filtered. The filtrate was concentrated under reduced pressure. Purification by flash chromatography (silica gel, petroleum ether:ethyl acetate=20:1 to 10:1 by vol) gave tert-butyl 4-(4-iodophenyl)-5-oxa-2-azabicyclo[2.2.2]octane-2-carboxylate as a yellow solid (0.25 g, yield 58%).

MS(ESI): 316.0 ([M-C$_4$H$_8$—CO$_2$+H]$^+$).

e) (RS)-5-Chloro-N-[4-(5-oxa-2-azabicyclo[2.2.2]octan-4-yl)phenyl]pyridin-2-amine To a solution of tert-butyl 4-(4-iodophenyl)-5-oxa-2-azabicyclo[2.2.2]octane-2-carboxylate (50 mg, 0.12 mmol) in 1,4-dioxane (2.0 ml) were added 2-amino-5chloropyridine (26 mg, 0.2 mmol, CAS: 1072-98-6), bis(diphenylphosphino)-9,9-dimethylxanthene (Xantphos, 12 mg, 0.02 mmol, CAS: 161265-03-8), tris(dibenzylidineacetone)dipalladium(0) (18 mg, 0.02 mmol, CAS: 51364-51-3), and Cs$_2$CO$_3$ (65 mg, 0.2 mmol, CAS: 534-17-8). The reaction mixture was stirred at 90° C. for 2 hours under N$_2$ atmosphere until LC-MS analysis indicated completion of the reaction. The mixture was cooled to room temperature and filtered. The filtrate was concentrated under reduced pressure. The residue was purified by prep-HPLC (mobile phase A: H$_2$O, B: CH$_3$CN with 0.1% NH$_3$.H$_2$O, C-18 column) to give tert-butyl 4-[4-[(5-chloro-2-pyridyl)amino]phenyl]-5-oxa-2-azabicyclo[2.2.2]octane-2-carboxylate as a white solid.

To a solution of tert-butyl 4-[4-[(5-chloro-2-pyridyl)amino]phenyl]-5-oxa-2-azabicyclo[2.2.2]octane-2-carboxylate in CH$_2$Cl$_2$ (2.0 ml) was added TFA (0.4 ml, CAS: 76-05-1). The reaction mixture was stirred at 0° C. for 4 hours. Volatiles were removed under reduced pressure. Purification by by prep-HPLC (mobile phase A: H$_2$O, B: CH$_3$CN with 0.1% TFA, C-18 column) gave (RS)-5-chloro-N-[4-(5-oxa-2-azabicyclo[2.2.2]octan-4-yl)phenyl]pyridin-2-amine (25 mg, 66% yield) as a yellow oil. MS (ESI): 317.9 ([{$^{37}$Cl}M+H]$^+$), 315.9 ([{$^{35}$Cl}M+H]$^+$).

$^1$H NMR (methanol-d$^4$, 400 MHz): δ 8.05 (d, 2H), 7.65 (m, 1H), 7.53 (d, 2H), 7.37 (d, 2H), 6.91 (d, 1H), 4.40 (d, 1H), 4.20 (d, 1H), 3.73 (s, 1H), 3.64 (d, 1H), 3.33 (d, 1H), 2.36-2.19 (m, 4H).

EXAMPLE 4

(RS)—N-[4-(5-Oxa-2-azabicyclo[2.2.2]octan-4-yl)phenyl]-5-(trifluoromethyl)pyridin-2-amine

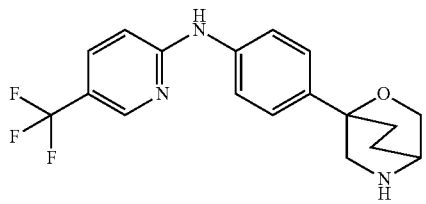 [SMILES: FC(F)(F)c1ccc(Nc2ccc(C34CCC(CO3)NC4)cc2)nc1]

The title compound was obtained in analogy to example 3 using 2-amino-5-(trifluoromethyl)pyridine (CAS: 74784-70-6) instead of 2-amino-5-chloropyridine in step (e). White solid. MS(ESI): 350.0 ([M+H]$^+$).

EXAMPLE 5

(RS)-4-Chloro-N-[4-(5-oxa-2-azabicyclo[2.2.2]octan-4-yl)phenyl]benzamide

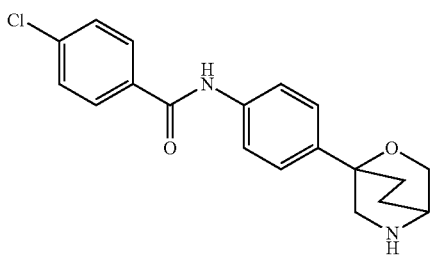 [SMILES: O=C(Nc1ccc(C23CCC(CO2)NC3)cc1)c1ccc(Cl)cc1]

To a solution of tert-butyl 4-(4-iodophenyl)-5-oxa-2-azabicyclo[2.2.2]octane-2-carboxylate (50 mg, 0.12 mmol) in 1,4-dioxane (2.0 ml) were added 4-chlorobenzamide (32 mg, 0.21 mmol, CAS: 619-56-7), Xantphos (12 mg, 0.02 mmol, CAS: 161265-03-8), tris(dibenzylidineacetone)dipalladium(0) (18 mg, 0.02 mmol, CAS: 51364-51-3), and Cs$_2$CO$_3$ (65 mg, 0.2 mmol, CAS: 534-17-8). The reaction mixture was stirred at 90° C. under N$_2$ atmosphere for 12 hours until LCMS indicated completion of the reaction. The residue was purified by prep-HPLC (mobile phase A: H$_2$O, B: CH$_3$CN with 0.1% NH$_3$.H$_2$O, C-18 column) to give tert-butyl 4-[4-[(4-chlorobenzoyl)amino]phenyl]-5-oxa-2-azabicyclo[2.2.2]octane-2-carboxylate as a brown solid.

To a solution of tert-butyl 4-[4-[(4-chlorobenzoyl)amino]phenyl]-5-oxa-2-azabicyclo[2.2.2]octane-2-carboxylate in CH$_2$Cl$_2$ (4.0 ml) was added TFA (0.5 ml, CAS: 76-05-1) at 0° C. under N$_2$ atmosphere. The reaction mixture was stirred at 0° C. for 4 hours until LCMS analysis indicated completion of the reaction. Volatiles were removed under reduced pressure.

Purification by prep-HPLC (mobile phase A: H$_2$O, B: CH$_3$CN with 0.1% TFA, C-18 column) gave (RS)-4-chloro-N-[4-(5-oxa-2-azabicyclo[2.2.2]octan-4-yl)phenyl]benzamide (21 mg, 51% yield) as a white solid. MS (ESI): 345.0 ([{$^{37}$Cl}M+H]$^+$), 343.0 ([{$^{35}$Cl}M+H]$^+$).

$^1$H NMR (methanol-d$^4$, 400 MHz): δ 7.94 (d, 2H), 7.73 (d, 2H), 7.53 (d, 2H), 7.46 (d, 2H), 4.42 (d, 1H), 4.23 (d, 1H), 3.83 (s, 1H), 3.67 (d, 1H), 3.50 (d, 1H), 2.38-2.21 (m, 4H).

EXAMPLE 6

3-Chloro-N-[4-(5-oxa-2-azabicyclo[2.2.2]octan-4-yl)phenyl]benzamide

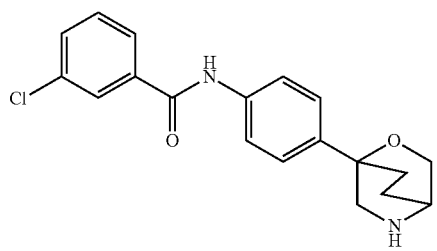 [SMILES: O=C(Nc1ccc(C23CCC(CO2)NC3)cc1)c1cccc(Cl)c1]

The title compound was obtained in analogy to example 5 using 3-chlorobenzamide (CAS: 618-48-4) instead of 4-chlorobenzamide. MS (ESI): 344.9 ([{$^{37}$Cl}M+H]$^+$), 342.9 ([{$^{35}$Cl}M+H]$^+$).

EXAMPLE 7

5-Chloro-N-[4-[(1S,4R)-5-oxa-2-azabicyclo[2.2.1]heptan-4-yl]phenyl]pyridin-2-amine

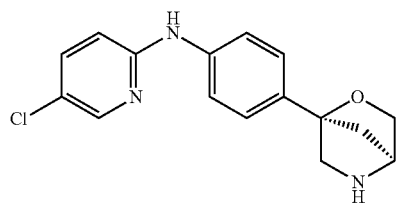 [SMILES: Clc1ccc(Nc2ccc([C@]34CN[C@H](CO3)C4)cc2)nc1]

a) (2S)-1-tert-Butoxycarbonyl-4-hydroxy-4-phenylpyrrolidine-2-carboxylic acid

A solution of N-Boc-4-oxo-L-proline (50 g, 0.22 mol, CAS: 84348-37-8) in anhydrous THF (500 mL) was added to phenylmagnesium bromide solution (1N in THF, 650 mL, CAS: 100-58-3) in anhydrous THF (500 mL) at 0° C. The reaction mixture was stirred at 0° C. for 15 min until TLC analysis indicated completion of the reaction. The reaction solution was quenched with saturated NH₄Cl solution (100 mL). The mixture was extracted with ethyl acetate (2×50 mL). The combined organic layers were washed with brine (50 mL), dried over Na₂SO₄, and concentrated under reduced pressure. Further drying under high vacuum gave crude (2S)-1-tert-butoxycarbonyl-4-hydroxy-4-phenyl-pyrrolidine-2-carboxylic acid (40 g, 59% yield) as a yellow solid.

¹H NMR (DMSO-d⁶, 400 MHz): δ 7.46-7.44 (m, 2H), 7.35-7.32 (m, 2H), 7.26 (m, 1H), 5.51 (s, 1H), 4.33-4.25 (m, 1H), 3.64-3.53 (m, 2H), 2.63-2.58 (m, 1H), 2.27-2.21 (m, 1H), 1.39 (s, 9H).

b) tert-Butyl (2S)-4-hydroxy-2-(hydroxymethyl)-4-phenyl-pyrrolidine-1-carboxylate To a solution of (2S)-1-tert-butoxycarbonyl-4-hydroxy-4-phenyl-pyrrolidine-2-carboxylic acid (40 g, 0.13 mol) in anhydrous THF (400 mL) was added borane tetrahydrofuran complex solution (390 mL, 0.39 mol, CAS: 14044-65-6) at 0° C. The reaction mixture was heated at reflux temperature for 3 hours until TLC analysis indicated completion of the reaction. The reaction mixture was quenched with MeOH (50 mL) and concentrated under reduced pressure. The residue was purified by flash chromatography (silica gel, CH₂Cl₂:MeOH=100:1 by vol) to give tert-butyl (2S)-4-hydroxy-2-(hydroxymethyl)-4-phenyl-pyrrolidine-1-carboxylate (28 g, yield: 74%) as a white solid.

¹HNMR (DMSO-d⁶, 400 MHz): δ 7.48 (m, 2H), 7.33 (m, 2H), 7.24 (m, 1H), 5.11 (s, 1H), 3.91-3.74 (m, 2H), 3.61-3.54 (m, 2H), 3.43 (d, 1H), 3.17 (d, 1H), 2.41-2.36 (m, 1H), 2.22-2.11 (m, 1H), 1.41 (s, 9H).

c) tert-Butyl (1S,4R)-4-phenyl-5-oxa-2-azabicyclo[2.2.1]heptane-2-carboxylate To a solution of tert-butyl (2S)-4-hydroxy-2-(hydroxymethyl)-4-phenyl-pyrrolidine-1-carboxylate (25 g, 80 mmol) in anhydrous toluene (300 mL) was added PPh₃ (96 g, 96 mmol, CAS: 603-35-0) and DIAD (27.5 g, 96 mmol, CAS: 2446-83-5) at 0° C. The mixture was stirred at room temperature under N₂ atmosphere overnight until TLC analysis indicated completion of the reaction. Volatiles were removed under reduce pressure. The residue was dissolved in tert-butyl methyl ether (500 mL) and filtered. The filtrate was concentrated under reduced pressure. Purification by flash chromatography (silica gel, petroleum ether:ethyl acetate=20:1 give tert-butyl (1S,4R)-4-phenyl-5-oxa-2-azabicyclo[2.2.1]heptane-2-carboxylate (13.5 g, 58% yield) as a white solid.

¹HNMR (DMSO-d⁶, 400 MHz): δ 7.49 (m, 2H), 7.40-7.35 (m, 3H), 4.64 (d, 1H), 4.08 (dd, 1H), 4.04 (s, 1H), 3.70-3.56 (m, 2H), 2.26 (d, 1H), 2.06 (d, 1H), 1.49 (d, 9H)

d) tert-Butyl (1S,4R)-4-(4-iodophenyl)-5-oxa-2-azabicyclo[2.2.1]heptane-2-carboxylate A solution of tert-butyl (1S,4R)-4-phenyl-5-oxa-2-azabicyclo[2.2.1]heptane-2-carboxylate (1.3 g, 4.7 mmol), [bis(trifluoroacetoxy)iodo]benzene (2.4 g, 5.6 mmol, CAS: 2712-78-9), and iodine (1.3 g, 5.2 mmol, CAS: 7553-56-2) in anhydrous CCl₄ (15 mL) was stirred at room temperature under N₂ atmosphere overnight. Then the solution was diluted with chloroform (200 mL) and washed with saturated aqueous NaHSO₃ (2×200 mL) and saturated aqueous NaCl (5×100 mL). The organic layer was concentrated under reduced pressure. The residue was purified by flash chromatography (silica gel, petroleum ether:ethyl acetate=20:1 by vol) to give tert-butyl (1S,4R)-4-(4-iodophenyl)-5-oxa-2-azabicyclo[2.2.1]heptane-2-carboxylate (500 mg, 26% yield) as a brown oil.

¹HNMR (CDCl₃, 400 MHz): δ 7.72 (d, 2H), 7.22 (d, 2H), 4.62 (d, 1H), 4.05 (dd, 1H), 4.02 (s, 1H), 3.57 (m, 2H), 2.22 (d, 1H), 1.99 (d, 1H), 1.49 (d, 9H).

e) 5-Chloro-N-[4-[(1S,4R)-5-oxa-2-azabicyclo[2.2.1]heptan-4-yl]phenyl]pyridin-2-amine To a solution of 2-amino-5-chloropyridine (175 mg, 1.35 mmol, CAS: 1072-98-6) and tert-butyl (1S,4R)-4-(4-iodophenyl)-5-oxa-2-azabicyclo[2.2.1]heptane-2-carboxylate (500 mg, 1.25 mmol) in dioxane (10 mL) were added Cs₂CO₃ (1.22 g, 3.75 mmol, CAS: 534-17-8), tris(dibenzylidineacetone)dipalladium(0) (100 mg, 0.125 mmol, CAS: 51364-51-3) and Xantphos (130 mg, 0.25 mmol, CAS: 161265-03-8). The reaction was stirred under N₂ atmosphere at 90° C. overnight until LCMS analysis indicated completion of the reaction. Volatiles were removed under reduce pressure. The residue was purified by flash chromatography (silica gel, petroleum ether:ethyl acetate=50:1 to 5:1 by vol) to give tert-butyl (1S,4R)-4-[4-[(5-chloro-2-pyridyl)amino]phenyl]-5-oxa-2-azabicyclo[2.2.1]heptane-2-carboxylate (80 mg) as a yellow oil.

To a solution of tert-butyl (1S,4R)-4-[4-[(5-chloro-2-pyridyl)amino]phenyl]-5-oxa-2-azabicyclo[2.2.1]heptane-2-carboxylate (80 mg) in anhydrous CH₂Cl₂ (1 mL) was added TFA (170 mg, 1.5 mmol, CAS: 76-05-1). The reaction mixture was stirred at room temperature for 2 hours. Volatiles were removed under reduced pressure. Water (10 mL) was added. Saturated NaHCO₃ solution was added to adjust pH to ~9. The mixture was extracted with ethyl acetate (3×20 mL). The combined organic layers were washed with brine, dried over Na₂SO₄, and concentrated under reduced pressure. The residue was purified by prep-HPLC (mobile phase A: H₂O, B: CH₃CN with 0.1% NH₃.H₂O, C-18 column) to give 5-chloro-N-[4-[(1S,4R)-5-oxa-2-azabicyclo[2.2.1]heptan-4-yl]phenyl]pyridin-2-amine (5 mg, 1.3% yield) as a white solid. MS (ESI): 304.1 ([{³⁷Cl}M+H]⁺), 302.1 ([{³⁵Cl}M+H]⁺).

¹H NMR (methanol-d⁴, 400 MHz): δ 8.08 (d, 1H), 7.60-7.51 (m, 3H), 7.39 (m 2H), 6.81 (d, 1H), 4.03 (m, 3H), 3.35-3.24 (m, 2H), 2.18 (m, 2H).

EXAMPLE 8

1-[4-[[(1S,4S)-5-Oxa-2-azabicyclo[2.2.1]heptan-4-yl]methyl]phenyl]-3-[4-(trifluoromethyl)phenyl]urea

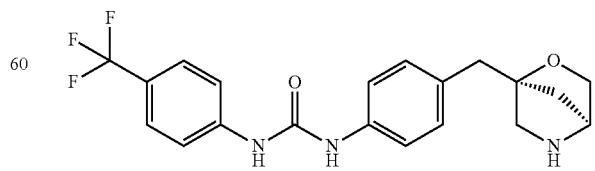

The title compound was obtained in analogy to example 1 using 4-(trifluoromethyl)phenyl isocyanate (CAS: 1548-

13-6) instead of 4-chlorophenyl isocyanate in step (g). White solid. MS (ESI): 392.0 ([M+H]⁺).

EXAMPLE 9

1-(2-Chlorophenyl)-3-[4-[[(1S,4S)-5-oxa-2-azabicyclo[2.2.1]heptan-4-yl]methyl]phenyl]urea

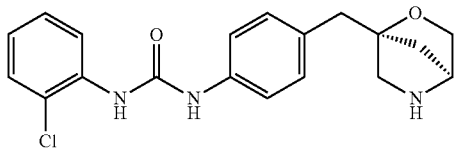 [SMILES: O=C(Nc1ccc(C[C@]23CN[C@H](CO2)C3)cc1)Nc1ccccc1Cl]

The title compound was obtained in analogy to example 1 using 2-chlorophenyl isocyanate (CAS: 3320-83-0) instead of 4-chlorophenyl isocyanate in step (g). White solid.

MS (ESI): 360.0 ([{³⁷Cl}M+H]⁺), 358.0 ([{³⁵Cl}M+H]⁺).

EXAMPLE 10

1-[4-[[(1S,4S)-5-Oxa-2-azabicyclo[2.2.1]heptan-4-yl]methyl]phenyl]-3-[3-(trifluoromethyl)phenyl]urea

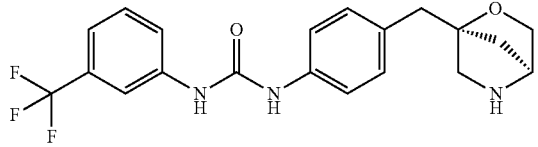 [SMILES: O=C(Nc1ccc(C[C@]23CN[C@H](CO2)C3)cc1)Nc1cccc(C(F)(F)F)c1]

The title compound was obtained in analogy to example 1 using 3-(trifluoromethyl)phenyl isocyanate (CAS: 329-01-1) instead of 4-chlorophenyl isocyanate in step (g). White solid. MS (ESI): 392.0 ([M+H]⁺).

EXAMPLE 11

(RS)-4-(Cyclopropylmethoxy)-N-[4-(5-oxa-2-azabicyclo[2.2.2]octan-4-yl)phenyl]benzamide

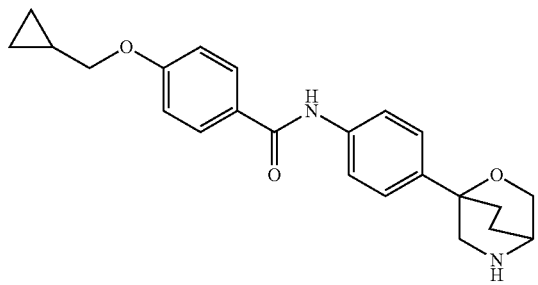 [SMILES: O=C(Nc1ccc(C23CCC(CO2)NC3)cc1)c1ccc(OCC2CC2)cc1]

a) 4-(Cyclopropylmethoxy)benzamide

To a solution of 4-(cyclopropylmethoxy)benzoic acid (384 mg, CAS: 355391-05-8), HATU (836 mg, CAS: 148893-10-1) and Et₃N (606 mg, CAS: 121-44-8) in DMF (2.0 mL) was added NH₃ in water (25%~28%, 1.0 mL) at room temperature. The reaction mixture was stirred overnight.

Volatiles were removed under reduced pressure. The mixture was purified through reverse phase chromatography (C-18 column, mobile phase: A, H₂O; B, CH₃CN with 0.5% NH₃.H₂O) to give 4-(cyclopropylmethoxy)benzamide as a white solid (275 mg, yield 72%). MS (ESI): 192.1 (M+H)⁺.

b) (RS)-4-(Cyclopropylmethoxy)-N-[4-(5-oxa-2-azabicyclo[2.2.2]octan-4-yl)phenyl]benzamide The title compound was obtained in analogy to example 5 using 4-(cyclopropylmethoxy)benzamide instead of 4-chlorobenzamide. White solid.

MS (ESI): 379.1 ([M+H]⁺).

EXAMPLE 12

(RS)-6-Ethoxy-N-[4-(5-oxa-2-azabicyclo[2.2.2]octan-4-yl)phenyl]pyridine-3-carboxamide

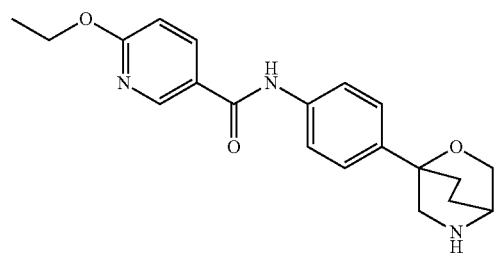 [SMILES: CCOc1ccc(C(=O)Nc2ccc(C34CCC(CO3)NC4)cc2)cn1]

The title compound was obtained in analogy to example 5 using 6-ethoxypyridine-3-carboxamide (CAS: 473693-84-4) instead of 4-chlorobenzamide. White solid. MS (ESI): 354.0 ([M+H]⁺).

EXAMPLE 13

(RS)—N-[4-(5-Oxa-2-azabicyclo[2.2.2]octan-4-yl)phenyl]-6-(2,2,2-trifluoroethoxy)pyridine-3-carboxamide

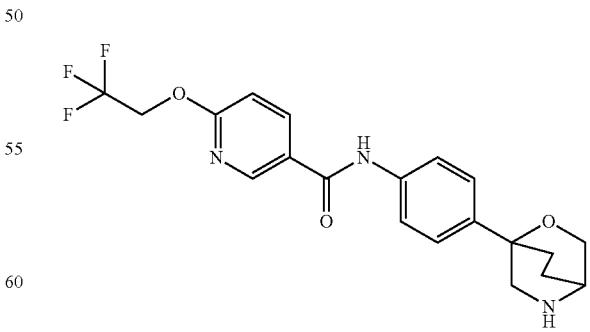

The title compound was obtained in analogy to example 5 using 6-(2,2,2-trifluoroethoxy)pyridine-3-carboxamide (CAS: 676533-51-0) instead of 4-chlorobenzamide. White solid. MS (ESI): 408.0 ([M+H]⁺).

EXAMPLE 14

(RS)-2-Cyclopropyl-N-[4-(5-oxa-2-azabicyclo[2.2.2]octan-4-yl)phenyl]pyrimidine-5-carboxamide

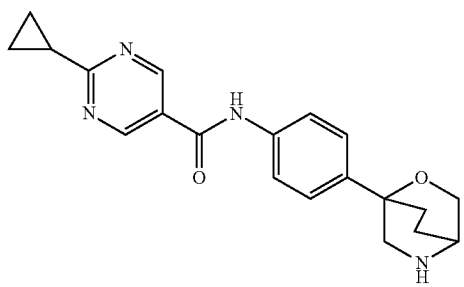 [SMILES: O=C(Nc1ccc(C23CCC(CO2)NC3)cc1)c1cnc(C2CC2)nc1]

a) 2-Cyclopropylpyrimidine-5-carboxamide

To a solution of 2-cyclopropylpyrimidine-5-carboxylic acid (328 mg, CAS: 648423-79-4), HATU (836 mg, CAS: 148893-10-1) and Et$_3$N (606 mg, CAS: 121-44-8) in DMF (2.0 mL) was added NH$_3$ in water (25%-28%, 1.0 mL) at room temperature. The reaction mixture was stirred overnight. Volatiles were removed under reduced pressure. The mixture was purified through reverse phase chromatography (C-18 column, mobile phase: A, H$_2$O; B, CH$_3$CN with 0.5% NH$_3$.H$_2$O) to give 2-cyclopropylpyrimidine-5-carboxamide as a white solid (241 mg, yield 74%). MS (ESI): 164.1 (M+H)$^+$.

b) (RS)-2-Cyclopropyl-N-[4-(5-oxa-2-azabicyclo[2.2.2]octan-4-yl)phenyl]pyrimidine-5-carboxamide The title compound was obtained in analogy to example 5 using 2-cyclopropylpyrimidine-5-carboxamide (CAS: 1447607-18-2) instead of 4-chlorobenzamide. White solid. MS (ESI): 351.0 ([M+H]$^+$).

EXAMPLE 15

4-Chloro-N-[4-[[(1S,4S)-5-oxa-2-azabicyclo[2.2.1]heptan-4-yl]methyl]phenyl]benzamide

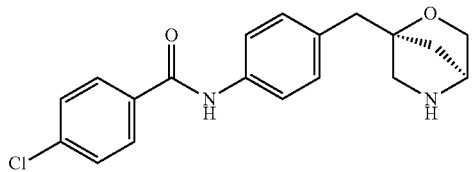 [SMILES: O=C(Nc1ccc(C[C@]23CN[C@H](CO2)C3)cc1)c1ccc(Cl)cc1]

To a solution of 4-chlorobenzoic acid (35.9 mg, 0.23 mmol, CAS: 74-11-3) in DMF (1 mL) were added HATU (96.2 mg, 0.253 mmol, CAS: 148893-10-1), N,N-diisopropylethylamine (89.1 mg, 0.69 mmol, CAS: 7087-68-5) and tert-butyl (1S,4S)-4-[(4-aminophenyl)methyl]-5-oxa-2-azabicyclo[2.2.1]heptane-2-carboxylate (70 mg, 0.23 mmol). The reaction mixture was stirred at room temperature overnight. Then the reaction mixture was diluted with CH$_2$Cl$_2$ (10 mL). The solution was washed with brine (20 mL), dried over Na$_2$SO$_4$, and concentrated under reduced pressure. The residue was dissolved in CH$_2$Cl$_2$ (1 mL) and TFA (1 mL). The solution was stirred at room temperature for 2 hours. The reaction solution was concentrated under reduced pressure. The residue was purified by prep-HPLC (mobile phase A: H$_2$O, B: CH$_3$CN with 0.1% TFA, C-18 column) to give RW-04-012-01 (26 mg, 33% of yield) as a yellow solid.

$^1$H NMR (400 MHz, Methanol-d$^4$): 7.92-7.90 (d, 2H), 7.65-7.63 (d, 2H), 7.54-7.52 (d, 2H), 7.31-7.28 (d, 2H), 4.33 (s, 1H), 4.00 (d, 1H), 3.91 (d, 1H), 3.25-3.16 (m, 4H), 2.01-1.92 (m, 2H). MS (ESI): 344.9 ([{$^{37}$Cl}M+H]$^+$), 342.9 ([{$^{35}$Cl}M+H]$^+$).

EXAMPLE 16

4-Chloro-N-[4-[[(1S,4S)-5-oxa-2-azabicyclo[2.2.1]heptan-4-yl]methyl]phenyl]-3-propyl-1H-pyrazole-5-carboxamide

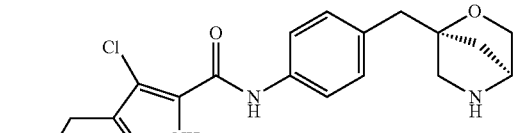

The title compound was obtained in analogy to example 15 using 4-chloro-5-propyl-1H-pyrazole-3-carboxylic acid (CAS: 1340578-20-2) instead of 4-chlorobenzoic acid. MS (ESI): 377.0 ([{$^{37}$Cl}M+H]$^+$), 375.0 ([{$^{35}$Cl}M+H]$^+$).

EXAMPLE 17

3-Chloro-N-[4-[[(1S,4S)-5-oxa-2-azabicyclo[2.2.1]heptan-4-yl]methyl]phenyl]benzamide

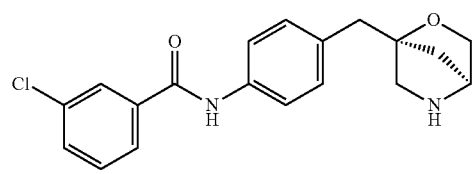 [SMILES: O=C(Nc1ccc(C[C@]23CN[C@H](CO2)C3)cc1)c1cccc(Cl)c1]

The title compound was obtained in analogy to example 15 using 3-chlorobenzoic acid (CAS: 535-80-8) instead of 4-chlorobenzoic acid.

MS (ESI): 345.0 ([{$^{37}$Cl}M+H]$^+$), 343.0 ([{$^{35}$Cl}M+H]$^+$).

EXAMPLE 18

N-[4-[[(1S,4S)-5-Oxa-2-azabicyclo[2.2.1]heptan-4-yl]methyl]phenyl]-2-(trifluoromethyl)pyridine-4-carboxamide

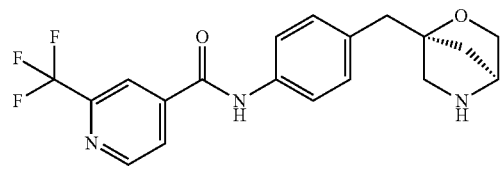 [SMILES: O=C(Nc1ccc(C[C@]23CN[C@H](CO2)C3)cc1)c1ccnc(C(F)(F)F)c1]

The title compound was obtained in analogy to example 15 using 2-(trifluoromethyl)pyridine-4-carboxylic acid (CAS: 131747-41-6) instead of 4-chlorobenzoic acid. MS (ESI): 378.0 ([M+H]$^+$).

EXAMPLE 19

4-Ethoxy-N-[4-[[(1 S,4S)-5-oxa-2-azabicyclo[2.2.1]heptan-4-yl]methyl]phenyl]benzamide

The title compound was obtained in analogy to example 15 using 4-ethoxybenzoic acid (CAS: 619-86-3) instead of 4-chlorobenzoic acid. MS (ESI): 353.0 ([M+H]$^+$).

EXAMPLE 20

5-Chloro-N-[4-[(1R,4S)-5-oxa-2-azabicyclo[2.2.1]heptan-4-yl]phenyl]pyridin-2-amine

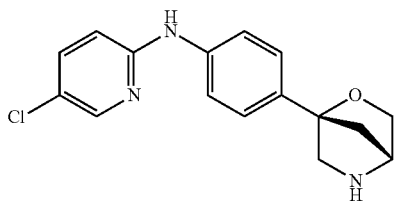 [SMILES: Clc1ccc(Nc2ccc([C@@]34CN[C@@H](CO3)C4)cc2)nc1]

a) tert-Butyl (1R,4S)-4-phenyl-5-oxa-2-azabicyclo[2.2.1]heptane-2-carboxylate tert-Butyl (1R,4S)-4-phenyl-5-oxa-2-azabicyclo[2.2.1]heptane-2-carboxylate can be prepared in analogy to tert-butyl (1S,4R)-4-phenyl-5-oxa-2-azabicyclo[2.2.1]heptane-2-carboxylate, which is the product in step (c) during preparation of example 7, using N-Boc-4-oxo-D-proline (CAS: 364077-84-9) instead of N-Boc-4-oxo-L-proline in step (a) during the preparation of example 7.
MS (ESI): 298.2 ([M+Na$^+$]), 220.1 ([M-C$_4$H$_8$+H]$^+$), 176.2 ([M-C$_4$H$_8$—CO$_2$+H]$^+$)
$^1$H NMR (methanol-d$^4$, 400 MHz): δ 7.50 (d, 2H), 7.36 (m, 3H), 4.61 (s, 1H), 4.01 (m, 2H), 3.62-3.31 (m, 2H), 2.31 (t, 1H), 2.07 (d, 1H), 1.49 (d, 9H).

b) (1R,4S)-4-Phenyl-5-oxa-2-azabicyclo[2.2.1]heptane

To a solution of tert-butyl (1R,4S)-4-phenyl-5-oxa-2-azabicyclo[2.2.1]heptane-2-carboxylate (500 mg, 1.82 mmol) in dry CH$_2$Cl$_2$ (5 mL) was added TFA (269 mg, 2.36 mmol, CAS: 76-05-1) at 0° C. The reaction mixture was stirred at room temperature for 2 hours. TLC analysis indicated the completion of the reaction. Volatiles were removed under reduced pressure. The residue was purified by prep-HPLC (C-18 column, mobile phase: A, H$_2$O; B, CH$_3$CN with 0.5% NH$_3$.H$_2$O) to give (1R,4S)-4-phenyl-5-oxa-2-azabicyclo[2.2.1]heptane (100 mg, 31% yield) as a yellow oil. MS (ESI): 176.2 ([M+H]$^+$)

c) 2,2,2-Trifluoro-1-[(1R,4S)-4-phenyl-5-oxa-2-azabicyclo[2.2.1]heptan-2-yl]ethanone To a solution of (1R,4S)-4-phenyl-5-oxa-2-azabicyclo[2.2.1]heptane (500 mg, 2.85 mmol) in CH$_2$Cl$_2$ (10 mL) were added trifluoroacetic anhydride (1.2 g, 5.71 mmol, CAS: 407-25-0) and Et$_3$N (865 mg, 8.55 mmol, CAS: 121-44-8). The reaction mixture was stirred at room temperature for 4 hours until LCMS analysis indicated completion of the reaction. Volatiles were removed under reduced pressure. The residue was purified by prep-HPLC (C-18 column, mobile phase: A, H$_2$O; B, CH$_3$CN with 0.5% NH$_3$.H$_2$O) to give 2,2,2-trifluoro-1-[(1R,4S)-4-phenyl-5-oxa-2-azabicyclo[2.2.1]heptan-2-yl]ethanone (200 mg, 26% yield) as a yellow oil. MS (ESI): 272.1 ([M+H]$^+$).

d) 2,2,2-Trifluoro-1-[(1R,4S)-4-(4-iodophenyl)-5-oxa-2-azabicyclo[2.2.1]heptan-2-yl]ethanone To a solution of 2,2,2-trifluoro-1-[(1R,4S)-4-phenyl-5-oxa-2-azabicyclo[2.2.1]heptan-2-yl]ethanone (200 mg, 0.74 mmol) in CCl$_4$ (5 mL), were added [bis(trifluoroacetoxy)iodo]benzene (594 mg, 0.81 mmol, CAS: 2712-78-9) and iodine (188 mg, 0.74 mmol, CAS: 7553-56-2). The reaction mixture was stirred at room temperature for 4 hours. LCMS indicated completion of the reaction. The mixture was diluted with chloroform (50 mL), washed with 5% aqueous NaHSO$_3$ solution and subsequently with 10% aqueous NaCl solution. The solution was dried over MgSO$_4$. Volatiles were removed under reduced pressure. The residue was purified by flash chromatography (silica gel, petroleum ether: ethyl acetate=50:1 to 5:1 by vol) to give 2,2,2-trifluoro-1-[(1R,4S)-4-(4-iodophenyl)-5-oxa-2-azabicyclo[2.2.1]heptan-2-yl]ethanone (160 mg, 54% yield) as a yellow solid. MS (ESI): 397.9 ([M+H]$^+$).

e) 5-Chloro-N-[4-[(1R,4S)-5-oxa-2-azabicyclo[2.2.1]heptan-4-yl]phenyl]pyridin-2-amine To an oven-dried schlenk tube were added 2,2,2-trifluoro-1-[(1R,4S)-4-(4-iodophenyl)-5-oxa-2-azabicyclo[2.2.1]heptan-2-yl]ethanone (80 mg, 0.20 mmol), 2-amino-5-chloropyridine (25 mg, 0.2 mmol, CAS: 1072-98-6), Xantphos (46 mg, 0.08 mmol, CAS: 161265-03-8), and tris(dibenzylideneacetone)dipalladium(0) (73 mg, 0.08 mmol, CAS: 51364-51-3). The tube was evacuated and flushed with nitrogen. Cs$_2$CO$_3$ (130 g, 0.4 mmol) and 1,4-dioxane (3 mL) were added under nitrogen. The tube was sealed. The reaction mixture was stirred at 90° C. for 24 hours until LCMS analysis indicated the completion of the reaction. The reaction mixture was diluted with water (20 mL) and extracted with ethyl acetate (3×20 mL). The combined organic layers were washed with brine (50 mL) and dried over Na$_2$SO$_4$. Volatiles were removed under reduced pressure. The residue was purified by prep-HPLC (mobile phase A: H$_2$O, B: CH$_3$CN with 0.1% NH$_3$.H$_2$O, C-18 column) to give 1-[(1R,4S)-4-[4-[(5-chloro-2-pyridyl)amino]phenyl]-5-oxa-2-azabicyclo[2.2.1]heptan-2-yl]-2,2,2-trifluoro-ethanone as a white solid. 1-[(1R,4S)-4-[4-[(5-Chloro-2-pyridyl)amino]phenyl]-5-oxa-2-azabicyclo[2.2.1]heptan-2-yl]-2,2,2-trifluoro-ethanone was dissolved in a mixture of MeOH (10 mL) and water (5 mL). K$_2$CO$_3$ (700 mg, 5.06 mmol) was added. The reaction mixture was stirred at room temperature for an hour, until LCMS indicated completion of the reaction. Volatiles were removed under reduced pressure. The residue was purified by prep-HPLC (mobile phase A: $H_2O$, B: $CH_3CN$ with 0.1% $NH_3.H_2O$, C-18 column) to give 5-chloro-N-[4-[(1R,4S)-5-oxa-2-azabicyclo[2.2.1]heptan-4-yl]phenyl]pyridin-2-amine (10 mg, 17% yield) as a waxy solid.

MS (ESI): 304.1 ([$\{^{37}Cl\}M+H]^+$), 302.1 ([$\{^{35}Cl\}M+H]^+$).

$^1$H NMR (methanol-d$^4$, 400 MHz): δ 8.07 (d, 1H), 7.53 (m, 3H), 7.28 (d, 2H), 6.80 (d, 1H), 3.97 (m, 2H), 3.79 (s, 1H), 3.16 (m, 2H), 2.12 (d, 1H), 2.03 (d, 1H).

EXAMPLE 21

4-Chloro-N-[4-[[(1R,4R)-5-oxa-2-azabicyclo[2.2.1]heptan-4-yl]methyl]phenyl]benzamide

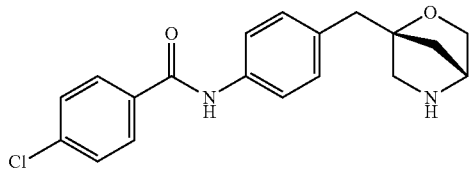 [SMILES: O=C(Nc1ccc(C[C@@]23CN[C@@H](CO2)C3)cc1)c1ccc(Cl)cc1]

a) (2R)-4-Benzyl-1-tert-butoxycarbonyl-4-hydroxy-pyrrolidine-2-carb oxylic acid

To a solution of benzylmagnesium bromide (1 M in THF, 436 mL, CAS: 1589-82-8) at 0° C. was added (R)-1-(tert-butoxycarbonyl)-4-oxopyrrolidine-2-carboxylic acid (60 g, 259 mmol, CAS: 364077-84-9) in THF (1000 mL) dropwise. The mixture was stirred at 0° C. for 3 hours until TLC analysis indicated complete consumption of the starting material. To the reaction mixture was added aqueous $NH_4Cl$ (1000 mL) at 0° C. The solution was allowed to warm to room temperature and extracted with EtOAc (1000 mL×2). The combined organic layers were washed with brine (1000 mL), dried over $Na_2SO_4$, and concentrated under reduced pressure. Purification by flash chromatography (silica gel, $CH_2Cl_2$/MeOH=100/1 to 20/1 by vol) gave (2R)-4-benzyl-1-tert-butoxycarbonyl-4-hydroxy-pyrrolidine-2-carboxylic acid (10 g, 12% yield) as a yellow oil.

b) tert-Butyl (2R)-4-benzyl-4-hydroxy-2-(hydroxymethyl)pyrrolidine-1-carboxylate To a solution of (2R)-4-benzyl-1-tert-butoxycarbonyl-4-hydroxy-pyrrolidine-2-carboxylic acid (5 g, 15.6 mmol) in THF (20 mL) was added borane tetrahydrofuran complex solution (1 M in THF, 50 mL, CAS: 14044-65-6) at 0° C. The reaction mixture was stirred at reflux temperature for 3 hours until TLC analysis indicated complete consumption of the starting material. To the reaction mixture was added MeOH (100 mL) at 0° C. The solution was stirred at room temperature for an hour. Volatiles were removed under reduced pressure. Purification by flash chromatography (silica gel, $CH_2Cl_2$/MeOH=100/1 to 20/1 by vol) gave tert-butyl (2R)-4-benzyl-4-hydroxy-2-(hydroxymethyl)pyrrolidine-1-carboxylate (1.5 g, 31% yield) as a yellow oil.

$^1$H NMR (400 MHz, Methanol-d$^4$): δ 7.32-7.22 (m, 5H), 3.86 (d, 2H), 3.61 (t, 1H), 3.51 (t, 1H), 3.29 (d, 1H), 2.88 (d, 2H), 2.25 (m, 1H), 1.88 (dd, 1H), 1.49 (s, 9H).

c) tert-Butyl (2R)-4-benzyl-4-hydroxy-2-(p-tolylsulfonyloxymethyl)pyrrolidine-1-carboxylate To a solution of tert-butyl (2R)-4-benzyl-4-hydroxy-2-(hydroxymethyl)pyrrolidine-1-carboxylate (2.8 g, 14.6 mmol) in pyridine (40 mL) was added p-toluenesulfonyl chloride (4.1 g, 13.3 mmol, CAS: 98-59-9) at 0° C. The solution was stirred at 30° C. for 48 hours. The reaction solution was poured into 10% aqueous citric acid solution (500 mL). The mixture was extracted with $CH_2Cl_2$ (500 mL×2). The combined organic layers were washed with brine (500 mL×3), dried over $Na_2SO_4$, and concentrated under reduced pressure. Purification by flash chromatography (silica gel, petroleum ether/ethyl acetate=30/1 to 10/1 by vol.) gave tert-butyl (2R)-4-benzyl-4-hydroxy-2-(p-tolylsulfonyloxymethyl)pyrrolidine-1-carboxylate (1.5 g, 25% yield) as a yellow oil. $^1$H NMR (400 MHz, Methanol-d$^4$): δ 7.78 (d, 2H), 7.46 (m, 2H), 7.31-7.23 (m, 5H), 4.22 (m, 2H), 3.93 (m, 1H), 3.46 (t, 1H), 3.11 (d, 1H), 2.86-2.54 (m, 2H), 2.47 (s, 3H), 2.03 (m, 1H), 1.90 (d, 1H), 1.40 (s, 9H).

d) tert-Butyl (1R,4R)-4-benzyl-5-oxa-2-azabicyclo[2.2.1]heptane-2-carboxylate

To a solution of tert-butyl (2R)-4-benzyl-4-hydroxy-2-(p-tolylsulfonyloxymethyl)pyrrolidine-1-carboxylate (1.05 g, 2.2 mmol) in THF (20 mL) was added 60% NaH (132 mg, 3.3 mmol) at 0° C. The solution was stirred at 25° C. overnight. To the reaction solution was added water (50 mL). The mixture was extracted with $CH_2Cl_2$ (100 mL×2). The combined organic layers were washed with brine (100 mL), dried over $Na_2SO_4$, and concentrated under reduced pressure. Purification by flash chromatography (silica gel, petroleum ether/ethyl acetate=15/1 to 3/1 by vol.) gave tert-butyl (1R,4R)-4-benzyl-5-oxa-2-azabicyclo[2.2.1]heptane-2-carboxylate (600 mg, 70% yield) as a white solid.

$^1$H NMR (400 MHz, Methanol-d$^4$): 7.28 (m, 5H), 4.41 (s, 1H), 3.81 (d, 2H), 3.26 (m, 1H), 3.12 (m, 3H), 1.77 (m, 1H), 1.69 (d, 1H), 1.46 (d, 9H).

e) (1R,4R)-4-[(4-Nitrophenyl)methyl]-5-oxa-2-azabicyclo[2.2.1]heptane

To a solution of tert-butyl (1R,4R)-4-benzyl-5-oxa-2-azabicyclo[2.2.1]heptane-2-carboxylate (1.26 g, 4.35 mmol) in trifluoroacetic acid (15 mL, CAS: 76-05-1) was added $KNO_3$ (1.32 g, 13 mmol) at 0° C. Then the solution was stirred at room temperature overnight. The reaction solution was diluted with water (100 mL). The pH was adjusted to 7-8 by addition of aqueous $NaHCO_3$ solution. The mixture was extracted with $CH_2Cl_2$/MeOH (10/1, 200 mL×3). The combined organic layers were washed with brine (200 mL), dried over $Na_2SO_4$, and concentrated under reduced pressure to give (1R,4R)-4-[(4-nitrophenyl)methyl]-5-oxa-2-azabicyclo[2.2.1]heptane (1.5 g, crude) as a yellow oil, which was used in the next step directly without purification.

f) tert-Butyl (1R,4R)-4-[(4-nitrophenyl)methyl]-5-oxa-2-azabicyclo[2.2.1]heptane-2-carboxylate To a solution of (1R,4R)-4-[(4-nitrophenyl)methyl]-5-oxa-2-azabicyclo[2.2.1]heptane (1.5 g, crude) in THF (45 mL) were added di-tert-butyl dicarbonate (2 g, 9 mmol, CAS: 24424-99-5) and K$_2$CO$_3$ (3 g, 22.5 mmol). The reaction mixture was stirred at room temperature overnight. The solution was diluted with ethyl acetate (100 mL). The mixture was washed with brine (50 mL) and dried over Na$_2$SO$_4$. Volatiles were removed under reduced pressure. Purification by flash chromatography (silica gel, petroleum ether/ethyl acetate=30/1 to 10/1 by vol.) gave tert-butyl (1R,4R)-4-[(4-nitrophenyl)methyl]-5-oxa-2-azabicyclo[2.2.1]heptane-2-carboxylate (590 mg, 43% yield over 2 steps) as a yellow solid. MS (ESI): 357.0 (M+Na$^+$), 279.0 (M-C$_4$H$_9$+H)$^+$.

$^1$H NMR (400 MHz, Methanol-d$^4$): 8.19 (d, 2H), 7.55 (d, 2H) 4.43 (s, 1H), 3.80 (s, 2H), 3.34-3.14 (m, 4H), 1.86 (t, 1H), 1.66 (d, 1H), 1.46 (d, 9H).

g) tert-Butyl (1R,4R)-4-[(4-aminophenyl)methyl]-5-oxa-2-azabicyclo[2.2.1]heptane-2-carboxylate To a solution of tert-butyl (1R,4R)-4-[(4-nitrophenyl)methyl]-5-oxa-2-azabicyclo[2.2.1]heptane-2-carboxylate (850 mg, 2.5 mmol) in MeOH (20 mL) was added 10% Pd/C (wet, 500 mg). The mixture was stirred at 30° C. under 50 psi H$_2$ overnight. The reaction mixture was filtered. The filtrate was concentrated under reduced pressure and dried further under high vacuum to give tert-butyl (1R,4R)-4-[(4-aminophenyl)methyl]-5-oxa-2-azabicyclo[2.2.1]heptane-2-carboxylate (750 mg, 97% yield) as a clear oil.

$^1$H NMR (400 MHz, Methanol-d$^4$): 7.01 (d, 2H), 6.69 (d, 2H) 4.40 (s, 1H), 3.80 (m, 2H), 3.24 (d, 1H), 3.13 (m, 1H), 2.97 (m, 2H), 1.71 (m, 2H), 1.47 (m, 9H).

h) 4-Chloro-N-[4-[[(1R,4R)-5-oxa-2-azabicyclo[2.2.1]heptan-4-yl]methyl]phenyl]benzamide tert-Butyl (1R,4R)-4-[(4-aminophenyl)methyl]-5-oxa-2-azabicyclo[2.2.1]heptane-2-carboxylate (40 mg, 0.13 mmol), 4-chlorobenzoic acid (27 mg, 0.14 mmol, CAS: 74-11-3), HATU (50 mg, 0.157 mmol, CAS: 148893-10-1) and N,N-diisopropylethylamine (50 mg, 0.47 mmol, CAS: 7087-68-5) were dissolved in DMF (1 mL). The solution was stirred at room temperature until LCMS analysis indicated complete consumption of the starting material. The solution was diluted with ethyl acetate (50 mL). The mixture was washed with H$_2$O (20 mL) and brine (10 mL). The combined organic layers were dried over Na$_2$SO$_4$, concentrated under reduced pressure, and dried under high vacuum to give crude tert-butyl (1R,4R)-4-[[4-[(4-chlorobenzoyl)amino]phenyl]methyl]-5-oxa-2-azabicyclo[2.2.1]heptane-2-carboxylate as a yellow oil, which was subsequently dissolved in CH$_2$Cl$_2$ (2 mL). TFA (1 mL) was added. The mixture was stirred at room temperature for an hour. Volatiles were removed under reduced pressure. Purification by prep-HPLC (mobile phase A: H$_2$O, B: CH$_3$CN with 0.1% TFA, C-18 column) gave 4-chloro-N-[4-[[(1R,4R)-5-oxa-2-azabicyclo[2.2.1]heptan-4-yl]methyl]phenyl]benzamide as a white solid. (21 mg, 47% yield).

MS (ESI): 345.0 ([$^{37}$Cl}M+H]$^+$), 343.0 ([$^{35}$Cl}M+H]$^+$).

$^1$H NMR (400 MHz, Methanol-d$^4$): 7.94 (d, 2H), 7.66 (d, 2H), 7.56 (d, 2H), 7.32 (d, 2H), 4.35 (s, 1H), 4.03 (d, 1H), 3.92 (d, 1H), 3.24-3.18 (m, 4H), 1.9 (dd, 2H).

EXAMPLE 22

1-[4-[[(1R,4R)-5-Oxa-2-azabicyclo[2.2.1]heptan-4-yl]methyl]phenyl]-3-[4-(trifluoromethyl)phenyl]urea

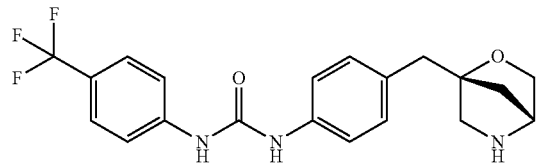 [SMILES: O=C(Nc1ccc(C[C@@]23CN[C@@H](CO2)C3)cc1)Nc1ccc(C(F)(F)F)cc1]

tert-Butyl (1R,4R)-4-[(4-aminophenyl)methyl]-5-oxa-2-azabicyclo[2.2.1]heptane-2-carboxylate (40 mg, 0.13 mmol), 4-(trifluoromethyl)phenyl isocyanate (22 mg, 0.14 mmol, CAS: 1548-13-6) and triethylamine (64 mg, 0.5 mmol, CAS: 121-44-8) were dissolved in CH$_2$Cl$_2$ (1 mL). The solution was stirred at room temperature until LCMS analysis indicated complete consumption of the starting materials. Water (10 mL) was added. The mixture was extracted with ethyl acetate (2×20 mL). The combined organic layers were dried over Na$_2$SO$_4$, concentrated under reduced pressure, and dried under high vacuum to give crude tert-butyl (1R,4R)-4-[[4-[[4-(trifluoromethyl)phenyl]carbamoylamino]phenyl]methyl]-5-oxa-2-azabicyclo[2.2.1]heptane-2-carboxylate as a yellow oil, which was then dissolved in CH$_2$Cl$_2$ (2 mL). TFA (1 mL) was added to the solution. The mixture was stirred at room temperature for an hour. Volatiles were removed under reduced pressure. The residual was dissolved in a mixture of CH$_2$Cl$_2$/CH$_3$OH (10:1 by vol.). The solution was washed with saturated NaHCO$_3$ solution (10 mL) and brine (5 mL). The organic layer was concentrated under reduced pressure. The residue was purified by prep-HPLC (mobile phase A: H$_2$O, B: CH$_3$CN with 0.1% TFA, C-18 column) to give 1-[4-[[(1R,4R)-5-Oxa-2-azabicyclo[2.2.1]heptan-4-yl]methyl]phenyl]-3-[4-(trifluoromethyl)phenyl]urea (11 mg, 25% yield) as a white solid. MS (ESI): 392.0 ([M+H]$^+$).

$^1$H NMR (400 MHz, Methanol-d$^4$): 7.65 (d, 2H), 7.59 (d, 2H), 7.43 (d, 2H), 7.25 (d, 2H), 4.34 (s, 1H), 4.02 (d, 1H), 3.91 (d, 1H), 3.23-3.14 (m, 4H), 1.98 (dd, 2H).

EXAMPLE 23

1-(4-Chlorophenyl)-3-[4-[[(1R,4R)-5-oxa-2-azabicyclo[2.2.1]heptan-4-yl]methyl]phenyl]urea

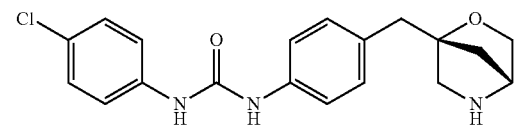 [SMILES: O=C(Nc1ccc(Cl)cc1)Nc1ccc(C[C@@]23CN[C@@H](CO2)C3)cc1]

The title compound was obtained in analogy to example 22 using 4-chlorophenyl isocyanate (CAS: 104-12-1) instead of 4-(trifluoromethyl)phenyl isocyanate.

MS (ESI): 360.0 ([$^{37}$Cl}M+H]$^+$), 358.0 ([$^{35}$Cl}M+H]$^+$).

EXAMPLE 24

1-(3-Chlorophenyl)-3-[4-[[(1R,4R)-5-oxa-2-azabicyclo[2.2.1]heptan-4-yl]methyl]phenyl]urea

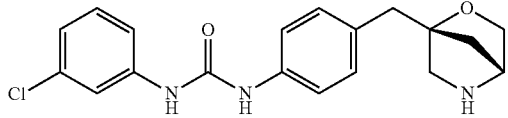 [SMILES: O=C(Nc1ccc(C[C@@]23CN[C@@H](CO2)C3)cc1)Nc1cccc(Cl)c1]

The title compound was obtained in analogy to example 22 using 3-chlorophenyl isocyanate (CAS: 2909-38-8) instead of 4-(trifluoromethyl)phenyl isocyanate.
MS (ESI): 360.0 ([{$^{37}$Cl}M+1-1]$^+$), 358.0 ([{$^{35}$Cl}M+1-1]$^+$).

EXAMPLE 25

4-(Cyclopropylmethoxy)-N-[4-[[(1S,4S)-5-oxa-2-azabicyclo[2.2.1]heptan-4-yl]methyl]phenyl]benzamide

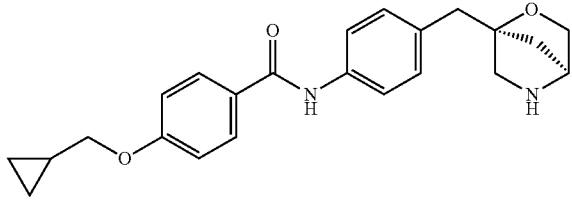 [SMILES: O=C(Nc1ccc(C[C@]23CN[C@H](CO2)C3)cc1)c1ccc(OCC2CC2)cc1]

The title compound was obtained in analogy to example 15 using 4-(cyclopropylmethoxy)benzoic acid (CAS: 355391-05-8) instead of 4-chlorobenzoic acid. MS (ESI): 379.0 ([M+1-1]$^+$).

EXAMPLE 26

6-Ethoxy-N-[4-[[(1S,4S)-5-oxa-2-azabicyclo[2.2.1]heptan-4-yl]methyl]phenyl]pyridine-3-carboxamide

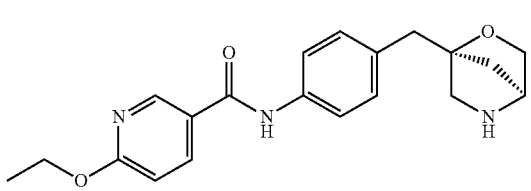 [SMILES: CCOc1ccc(C(=O)Nc2ccc(C[C@]34CN[C@H](CO3)C4)cc2)cn1]

The title compound was obtained in analogy to example 15 using 6-ethoxy-nicotinic acid (CAS: 97455-65-7) instead of 4-chlorobenzoic acid. MS (ESI): 354.0 ([M+1-1]$^+$).

EXAMPLE 27

N-[4-[[(1S,4S)-5-Oxa-2-azabicyclo[2.2.1]heptan-4-yl]methyl]phenyl]-6-(2,2,2-trifluoroethoxy)pyridine-3-carboxamide

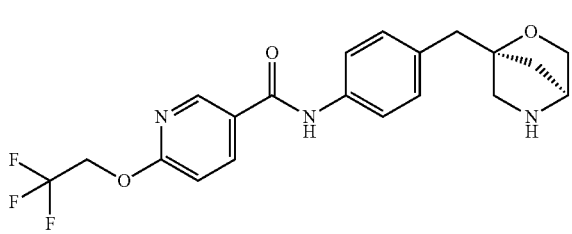 [SMILES: O=C(Nc1ccc(C[C@]23CN[C@H](CO2)C3)cc1)c1ccc(OCC(F)(F)F)nc1]

The title compound was obtained in analogy to example 15 using 6-(2,2,2-trifluoroethoxy)nicotinic acid (CAS: 175204-90-7) instead of 4-chlorobenzoic acid. MS (ESI): 408.0 ([M+H]$^+$).

EXAMPLE 28

2-Cyclopropyl-N-[4-[[(1S,4S)-5-oxa-2-azabicyclo[2.2.1]heptan-4-yl]methyl]phenyl]pyrimidine-5-carboxamide

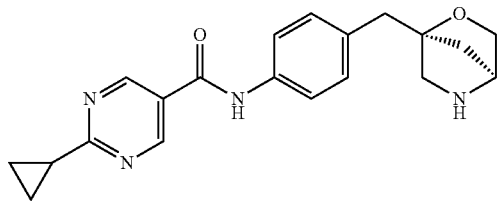 [SMILES: O=C(Nc1ccc(C[C@]23CN[C@H](CO2)C3)cc1)c1cnc(C2CC2)nc1]

The title compound was obtained in analogy to example 15 using 2-cyclopropyl-5-pyrimidinecarboxylic acid (CAS: 648423-79-4) instead of 4-chlorobenzoic acid. MS (ESI): 351.0 ([M+H]$^+$).

EXAMPLE 29

4-Chloro-3-cyclopropyl-N-[4-[[(1S,4S)-5-oxa-2-azabicyclo[2.2.1]heptan-4-yl]methyl]phenyl]-1H-pyrazole-5-carboxamide

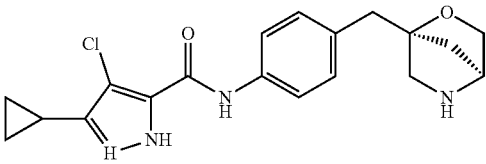

The title compound was obtained in analogy to example 15 using 4-chloro-5-cyclopropyl-2H-pyrazole-3-carboxylic acid (CAS: 1291275-83-6) instead of 4-chlorobenzoic acid. MS (ESI): 375.0 ([{$^{37}$Cl}M+H]$^+$), 373.0 ([{$^{35}$Cl}M+H]$^+$).

EXAMPLE 30

5-Chloro-N-[4-[[(1S,4S)-5-oxa-2-azabicyclo[2.2.1]heptan-4-yl]methyl]phenyl]pyridin-2-amine

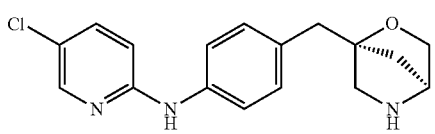 [SMILES: Clc1ccc(Nc2ccc(C[C@]34CN[C@H](CO3)C4)cc2)nc1]

To a solution of tert-butyl (1S,4S)-4-[(4-aminophenyl)methyl]-5-oxa-2-azabicyclo[2.2.1]heptane-2-carboxylate (70 mg, 0.23 mmol) and 2-bromo-5-chloropyridine (44 mg, 0.23 mmol, CAS: 40473-01-6) in dioxane (3 mL) were added Xantphos (40 mg, 0.07 mmol CAS: 161265-03-8) and tris(dibenzylidineacetone)dipalladium(0) (21 mg, 0.023 mmol, CAS: 51364-51-3). The mixture was stirred at 90° C. under N$_2$ atmosphere overnight. The solution was diluted with CH$_2$Cl$_2$ (10 mL). The solution was washed with brine (20 mL), dried over Na$_2$SO$_4$, and concentrated under reduced pressure. The residue was dissolved in a mixture of CH$_2$Cl$_2$ (1 mL) and TFA (1 mL). The solution was stirred at room temperature for 3 hours. Volatiles were removed under reduced pressure. The residue was purified by prep-HPLC (mobile phase A: H$_2$O, B: CH$_3$CN with 0.1% TFA, C-18 column) to give the title compound (28 mg, 39%=yield) as a white solid.

$^1$H NMR (400 MHz, Methanol-d$^4$): δ 8.04 (d, 1H), 7.58 (dd, 1H), 7.48 (d, 2H), 7.23 (d, 2H), 6.83 (d, 1H), 4.32 (s, 1H), 4.00 (d, 1H), 3.90 (dd, 1H), 3.24-3.12 (m, 4H), 1.96 (dd, 2H).

MS (ESI): 318.0 ([{$^{37}$Cl}M+H]$^+$), 316.0 ([{$^{35}$Cl}M+H]$^+$).

EXAMPLE 31

N-[4-[[(1S,4S)-5-Oxa-2-azabicyclo[2.2.1]heptan-4-yl]methyl]phenyl]-5-(trifluoromethyl)pyridin-2-amine

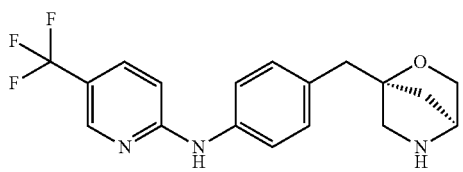 [SMILES: FC(F)(F)c1ccc(Nc2ccc(C[C@]34CN[C@H](CO3)C4)cc2)nc1]

The title compound was obtained in analogy to example 30 using 2-bromo-5-(trifluoromethyl)pyridine (CAS: 50488-42-1) instead of 2-bromo-5-chloropyridine. MS (ESI): 350.0 ([M+H]$^+$).

EXAMPLE 32

N-[4-[[(1S,4S)-5-Oxa-2-azabicyclo[2.2.1]heptan-4-yl]methyl]phenyl]-5-(trifluoromethyl)pyrazin-2-amine

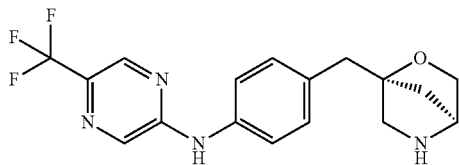 [SMILES: FC(F)(F)c1cnc(Nc2ccc(C[C@]34CN[C@H](CO3)C4)cc2)cn1]

The title compound was obtained in analogy to example 30 using 2-chloro-5-(trifluoromethyl)pyrazine (CAS: 799557-87-2) instead of 2-bromo-5-chloropyridine. MS (ESI): 351.0 ([M+H]$^+$).

EXAMPLE 33

N-[4-[[(1S,4S)-5-Oxa-2-azabicyclo[2.2.1]heptan-4-yl]methyl]phenyl]-5-(trifluoromethyl)pyrimidin-2-amine

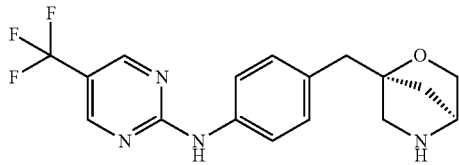 [SMILES: FC(F)(F)c1cnc(Nc2ccc(C[C@]34CN[C@H](CO3)C4)cc2)nc1]

The title compound was obtained in analogy to example 30 using 2-chloro-5-(trifluoromethyl)pyrimidine (CAS: 69034-12-4) instead of 2-bromo-5-chloropyridine. MS (ESI): 351.0 ([M+H]$^+$).

EXAMPLE 34

(RS)-4-Chloro-N-[4-(5-oxa-2-azabicyclo[2.2.2]octan-4-yl)phenyl]-3-propyl-1H-pyrazole-5-carboxamide

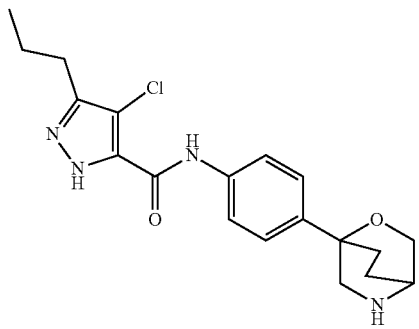 [SMILES: CCCc1n[nH]c(C(=O)Nc2ccc(C34CCC(CO3)NC4)cc2)c1Cl]

a) tert-Butyl 4-[4-(benzhydrylideneamino)phenyl]-5-oxa-2-azabicyclo[2.2.2]octane-2-carboxylate To a solution of tert-butyl 4-(4-iodophenyl)-5-oxa-2-azabicyclo[2.2.2]octane-2-carboxylate (300 mg, 0.72 mmol) in 1,4-dioxane (6.0 ml) were added benzophenone imine (157 mg, 0.87 mmol, CAS: 1013-88-3), bis(diphenylphosphino)-9,9-dimethylxanthene (Xantphos, 83 mg, 0.144 mmol, CAS: 161265-03-8), tris(dibenzylideneacetone)dipalladium(0) (132 mg, 0.144 mmol, CAS: 51364-51-3) and Cs$_2$CO$_3$ (469 mg, 1.44 mmol, CAS: 534-17-8). The reaction mixture was stirred under N$_2$ atmosphere at 90° C. overnight. The mixture was diluted with ethyl acetate (100 mL) and filtered. The filtrate was washed with water (20 mL) and brine (20 mL). Volatiles were removed under reduced pressure. Purification by preparative TLC (silica gel, petroleum ether:ethyl acetate=4:1 by vol) gave tert-butyl 4-[4-(benzhydrylideneamino)phenyl]-5-oxa-2-azabicyclo[2.2.2]octane-2-carboxylate (339 mg, >99% yield) as a yellow oil. MS(ESI): 469.3 ([M+H]$^+$).

b) tert-Butyl 4-(4-aminophenyl)-5-oxa-2-azabicyclo[2.2.2]octane-2-carboxylate

To a solution of tert-butyl 4-[4-(benzhydrylideneamino)phenyl]-5-oxa-2-azabicyclo[2.2.2]octane-2-carboxylate (339 mg, 0.72 mmol) in methanol (4 mL) were added hydroxylamine hydrochloride (250 mg, 3.6 mmol, CAS: 5470-11-1) and sodium acetate (593 mg, 7.2 mmol, CAS: 127-09-3). The reaction mixture was stirred at room temperature overnight. The solution was filtered. The filtrate was concentrated under reduced pressure. Purification by prep-HPLC (mobile phase A: H$_2$O, B: CH$_3$CN with 0.1% NH$_3$.H$_2$O, C-18 column) gave tert-butyl 4-(4-aminophenyl)-5-oxa-2-azabicyclo[2.2.2]octane-2-carboxylate (70 mg, 32% yield) as a white solid. MS(ESI): 305.2 ([M+H]$^+$).

c) (RS)-4-Chloro-N-[4-(5-oxa-2-azabicyclo[2.2.2]octan-4-yl)phenyl]-3-propyl-1H-pyrazole-5-carboxamide To a solution of tert-butyl 4-(4-aminophenyl)-5-oxa-2-azabicyclo[2.2.2]octane-2-carboxylate (20 mg, 0.063 mmol)

in anhydrous DMF (1 mL) were added HATU (38 mg, 0.1 mmol, CAS: 148893-10-1) and DIPEA (26 mg, 0.2 mmol, CAS: 7087-68-5). The mixture was stirred at room temperature for 30 minutes. 4-Chloro-5-propyl-1H-pyrazole-3-carboxylic acid (38 mg, 0.2 mmol, CAS: 80194-69-0) was added. The reaction mixture was stirred at room temperature for 2 hours until LCMS analysis indicated the completion of the reaction. Volatiles were removed under reduced pressure. The residue was dissolved in $CH_2Cl_2$ (20 mL), then washed with water and brine. The organic layer was concentrated under reduced pressure and dried under high vacuum to give crude tert-butyl 4-[4-[(4-chloro-3-propyl-1H-pyrazole-5-carbonyl)amino]phenyl]-5-oxa-2-azabicyclo[2.2.2]octane-2-carboxylate as a yellow solid, which was used directly in the next step.

To a solution of crude tert-butyl 4-[4-[(4-chloro-3-propyl-1H-pyrazole-5-carbonyl)amino]phenyl]-5-oxa-2-azabicyclo[2.2.2]octane-2-carboxylate in dry $CH_2Cl_2$ (2 mL) was added TFA (0.5 mL, CAS: 76-05-1). The mixture was stirred at room temperature for 30 minutes. Volatiles were removed under reduce pressure. The residue was purified by Prep-HPLC (mobile phase A: $H_2O$, B: $CH_3CN$ with 0.1% TFA, C-18 column) to give (RS)-4-chloro-N-[4-(5-oxa-2-azabicyclo[2.2.2]octan-4-yl)phenyl]-3-propyl-1H-pyrazole-5-carboxamide (16 mg, 68% yield) as a white solid. MS (ESI): 375.0 ($[\{^{37}Cl\}M+H]^+$), 377.0 ($[\{^{35}Cl\}M+H]^+$).

$^1$H NMR (methanol-$d^4$, 400 MHz): δ 7.74 (d, 2H), 7.40 (d, 2H), 4.42 (d, 1H), 4.23 (d, 1H), 3.75 (s, 1H), 3.66 (m, 1H), 3.50 (m, 1H), 2.71 (t, 2H), 2.38-2.23 (m, 4H), 1.73 (m, 2H), 0.99 (t, 3H).

EXAMPLE 35

(RS)-2-Ethyl-N-[4-(5-oxa-2-azabicyclo[2.2.2]octan-4-yl)phenyl]pyrimidine-5-carboxamide

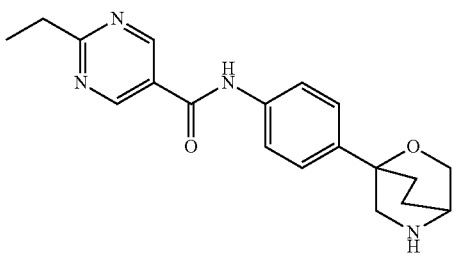 [SMILES: CCc1ncc(C(=O)Nc2ccc(C34CCC(CO3)NC4)cc2)cn1]

a) 2-Ethylpyrimidine-5-carboxamide

To a solution of 2-ethylpyrimidine-5-carboxylic acid (304 mg, CAS: 72790-16-0), HATU (836 mg, CAS: 148893-10-1) and $Et_3N$ (606 mg, CAS: 121-44-8) in DMF (2.0 mL) was added $NH_3$ in water (25%-28%, 1.0 mL) at room temperature. The reaction mixture was stirred overnight. Volatiles were removed under reduced pressure. The mixture was purified through reverse phase chromatography (C-18 column, mobile phase: A, $H_2O$; B, $CH_3CN$ with 0.5% $NH_3.H_2O$) to give 2-ethylpyrimidine-5-carboxamide as a white solid (120 mg, yield 40%). MS (ESI): 152.2 $(M+H)^+$.

b) (RS)-2-Ethyl-N-[4-(5-oxa-2-azabicyclo[2.2.2]octan-4-yl)phenyl]pyrimidine-5-carboxamide The title compound was obtained in analogy to example 5 using 6-(2,2,2-trifluoroethoxy)pyridine-3-carboxamide (CAS: 676533-51-0) instead of 4-chlorobenzamide. Waxy solid. MS (ESI): 339.0 ($[M+H]^+$).

EXAMPLE 36

N-[4-(5-Oxa-2-azabicyclo[2.2.2]octan-4-yl)phenyl]-2-(trifluoromethyl)pyrimidin-4-amine

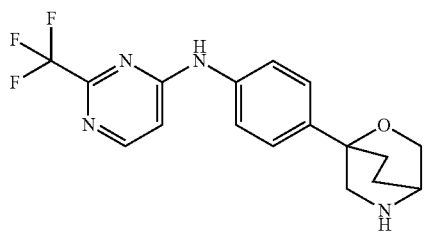 [SMILES: FC(F)(F)c1nccc(Nc2ccc(C34CCC(CO3)NC4)cc2)n1]

The title compound was obtained in analogy to example 3 using 2-(trifluoromethyl)pyrimidin-4-amine (CAS: 672-42-4) instead of 2-amino-5-chloropyridine in step (e). White solid. MS(ESI): 351.0 ($[M+H]^+$).

EXAMPLE 37

(RS)—N-[4-(5-Oxa-2-azabicyclo[2.2.2]octan-4-yl)phenyl]-2-(trifluoromethyl)pyridine-4-carboxamide

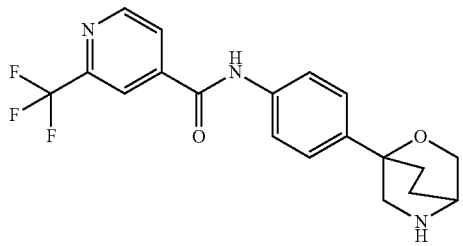 [SMILES: O=C(Nc1ccc(C23CCC(CO2)NC3)cc1)c1ccnc(C(F)(F)F)c1]

a) 2-(Trifluoromethyl)pyridine-4-carboxamide

To a solution of 2-(trifluoromethyl)pyridine-4-carboxylic acid (382 mg, 2.0 mmol, CAS: 131747-41-6), HATU (836 mg, 2.2 mmol, CAS: 148893-10-1) and $Et_3N$ (606 mg, 6.0 mmol, CAS: 121-44-8) in DMF (2.0 mL) was added $NH_3$ in water (25%-28%, 1.0 mL) at room temperature. The reaction mixture was stirred at room temperature overnight. The reaction was complete as detected by LCMS. The mixture was purified through reverse phase chromatography (C-18 column, mobile phase: A, $H_2O$; B, $CH_3CN$ with 0.5% $NH_3.H_2O$) to give 2-(trifluoromethyl)pyridine-4-carboxamide as a white solid (228 mg, yield 60%). White solid. MS (ESI): 191.0 ($[M+H]^+$).

b) (RS)—N-[4-(5-Oxa-2-azabicyclo[2.2.2]octan-4-yl)phenyl]-2-(trifluoromethyl)pyridine-4-carboxamide The title compound was obtained in analogy to example 5 using 2-(trifluoromethyl)pyridine-4-carboxamide instead of 4-chlorobenzamide. White solid. MS (ESI): 378.0 ($[M+H]^+$).

EXAMPLE 38

3-Isopropyl-N-[4-[[(1S,4S)-5-oxa-2-azabicyclo[2.2.1]heptan-4-yl]methyl]phenyl]-1H-pyrazole-5-carboxamide

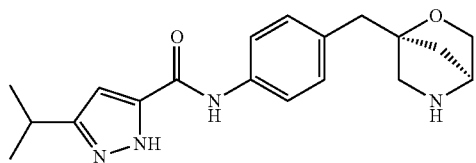 [SMILES: CC(C)c1cc(C(=O)Nc2ccc(C[C@]34CN[C@H](CO3)C4)cc2)[nH]n1]

The title compound was obtained in analogy to example 15 using 3-isopropylpyrazole-5-carboxylic acid (CAS: 92933-47-6) instead of 4-chlorobenzoic acid.

MS (ESI): 341.0 ([M+H]$^+$).

EXAMPLE 39

3-Chloro-N-[4-[[(1R,4R)-5-oxa-2-azabicyclo[2.2.1]heptan-4-yl]methyl]phenyl]benzamide

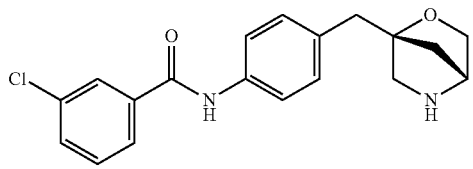 [SMILES: O=C(Nc1ccc(C[C@@]23CN[C@@H](CO2)C3)cc1)c1cccc(Cl)c1]

The title compound was obtained in analogy to example 21 using 3-chlorobenzoic acid (CAS: 535-80-8) instead of 4-chlorobenzoic acid in step (h).

MS (ESI): 345.0 ([{$^{37}$Cl}M+H]$^+$), 343.0 ([{$^{35}$Cl}M+H]$^+$).

EXAMPLE 40

N-[4-[[(1R,4R)-5-Oxa-2-azabicyclo[2.2.1]heptan-4-yl]methyl]phenyl]-2-(trifluoromethyl)pyridine-4-carboxamide

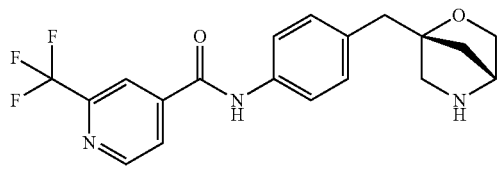 [SMILES: O=C(Nc1ccc(C[C@@]23CN[C@@H](CO2)C3)cc1)c1ccnc(C(F)(F)F)c1]

The title compound was obtained in analogy to example 21 using 2-(trifluoromethyl)pyridine-4-carboxylic acid (CAS: 131747-41-6) instead of 4-chlorobenzoic acid in step (h).

MS (ESI): 378.0 ([M+H]$^+$).

EXAMPLE 41

4-Chloro-N-[4-[[(1R,4R)-5-oxa-2-azabicyclo[2.2.1]heptan-4-yl]methyl]phenyl]-3-propyl-1H-pyrazole-5-carboxamide

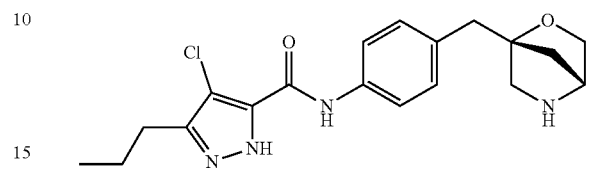

The title compound was obtained in analogy to example 21 using 4-chloro-3-propyl-1H-pyrazole-5-carboxylic acid (CAS: 1340578-20-2) instead of 4-chlorobenzoic acid in step (h).

MS (ESI): 377.1 ([{$^{37}$Cl}M+H]$^+$), 375.1 ([{$^{35}$Cl}M+H]$^+$).

EXAMPLE 42

5-Chloro-N-[4-[[(1R,4R)-5-oxa-2-azabicyclo[2.2.1]heptan-4-yl]methyl]phenyl]pyridin-2-amine

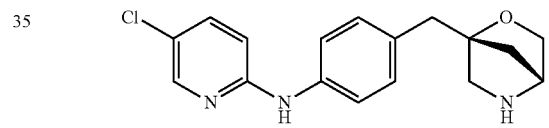

A mixture of tert-butyl (1R,4R)-4-[(4-aminophenyl)methyl]-5-oxa-2-azabicyclo[2.2.1]heptane-2-carboxylate (70 mg, 0.23 mmol), 2-bromo-5-chloropyridine (46 mg, 0.25 mmol, CAS: 40473-01-6), Xantphos (26 mg, 0.046 mmol, CAS: 161265-03-8), tris(dibenzylidineacetone)dipalladium(0) (21 mg, 0.023 mmol, CAS: 51364-51-3) and Cs$_2$CO$_3$ (224 mg, 0.69 mmol) in dioxane (5 mL) was stirred at 90° C. for 12 hours under N$_2$ atmosphere. The reaction mixture was cooled to room temperature and diluted with water (50 mL). The mixture was extracted with ethyl acetate (50 mL×2) and washed with water (50 mL). The organic layer was concentrated under reduced pressure and dried under high vacuum to give a yellow solid which was dissolved in the mixture of CH$_2$Cl$_2$ (3 mL) and TFA (1 mL). The reaction mixture was stirred at room temperature for an hour. Volatiles were removed under reduced pressure. The residue was purified by prep-HPLC (mobile phase A: H$_2$O, B: CH$_3$CN with 0.1% TFA, C-18 column) to give the title compound as a white solid (25 mg, 34% yield) MS (ESI): 318.0 ([{$^{37}$Cl}M+H]$^+$), 316.1 ([{$^{35}$Cl}M+H]$^+$).

$^1$H NMR (400 MHz, Methanol-d$^4$): 8.05 (d, 1H), 7.69 (dd, 1H), 7.47 (d, 2H), 7.29 (d, 2H), 6.93 (d, 1H), 4.35 (s, 1H), 4.03 (d, 1H), 91 (d, 1H), 3.23~3.16 (m, 4H), 1.99 (t, 2H).

EXAMPLE 43

1-(2-Chlorophenyl)-3-[4-[[(1R,4R)-5-oxa-2-azabicyclo[2.2.1]heptan-4-yl]methyl]phenyl]urea

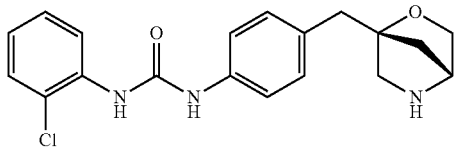 [SMILES: O=C(Nc1ccc(C[C@@]23CN[C@@H](CO2)C3)cc1)Nc1ccccc1Cl]

The title compound was obtained in analogy to example 22 using 2-chlorophenyl isocyanate (CAS: 3320-83-0) instead of 4-(trifluoromethyl)phenyl isocyanate.

MS (ESI): 360.0 ([{$^{37}$Cl}M+H]$^+$), 358.0 ([{$^{35}$Cl}M+H]$^+$).

EXAMPLE 44

1-[4-[[(1R,4R)-5-Oxa-2-azabicyclo[2.2.1]heptan-4-yl]methyl]phenyl]-3-[3-(trifluoromethyl)phenyl]urea

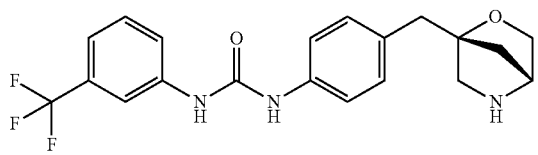 [SMILES: O=C(Nc1ccc(C[C@@]23CN[C@@H](CO2)C3)cc1)Nc1cccc(C(F)(F)F)c1]

The title compound was obtained in analogy to example 22 using 3-(trifluoromethyl)phenyl isocyanate (CAS: 329-01-1) instead of 4-(trifluoromethyl)phenyl isocyanate.

MS (ESI): 392.0 ([M+H]$^+$).

EXAMPLE 45

4-(Cyclopropylmethoxy)-N-[4-[[(1R,4R)-5-oxa-2-azabicyclo[2.2.1]heptan-4-yl]methyl]phenyl]benzamide

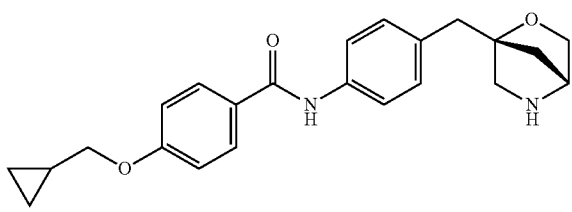 [SMILES: O=C(Nc1ccc(C[C@@]23CN[C@@H](CO2)C3)cc1)c1ccc(OCC2CC2)cc1]

The title compound was obtained in analogy to example 21 using 4-(cyclopropylmethoxy)benzoic acid (CAS: 355391-05-8) instead of 4-chlorobenzoic acid in step (h). MS (ESI): 379.1 ([M+H]$^+$).

EXAMPLE 46

6-Ethoxy-N-[4-[[(1R,4R)-5-oxa-2-azabicyclo[2.2.1]heptan-4-yl]methyl]phenyl]pyridine-3-carboxamide

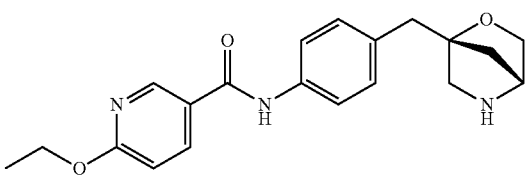 [SMILES: CCOc1ccc(C(=O)Nc2ccc(C[C@@]34CN[C@@H](CO3)C4)cc2)cn1]

The title compound was obtained in analogy to example 21 using 6-ethoxynicotinic acid (CAS: 97455-65-7) instead of 4-chlorobenzoic acid in step (h).

MS (ESI): 354.0 ([M+H]$^+$).

EXAMPLE 47

N-[4-[[(1R,4R)-5-Oxa-2-azabicyclo[2.2.1]heptan-4-yl]methyl]phenyl]-6-(2,2,2-trifluoroethoxy)pyridine-3-carboxamide

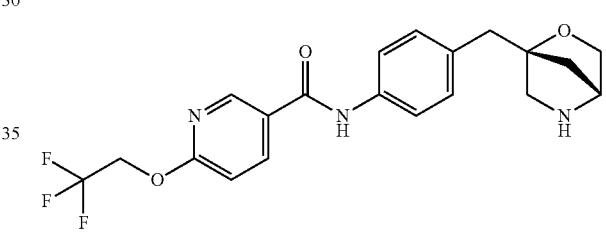

The title compound was obtained in analogy to example 21 using 6-(2,2,2-trifluoroethoxy)nicotinic acid (CAS: 175204-90-7) instead of 4-chlorobenzoic acid in step (h).
MS (ESI): 408.0 ([M+H]$^+$).

EXAMPLE 48

4-Chloro-3-cyclopropyl-N-[4-[[(1R,4R)-5-oxa-2-azabicyclo[2.2.1]heptan-4-yl]methyl]phenyl]-1H-pyrazole-5-carboxamide

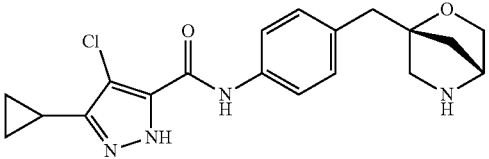 [SMILES: O=C(Nc1ccc(C[C@@]23CN[C@@H](CO2)C3)cc1)c1[nH]nc(C2CC2)c1Cl]

The title compound was obtained in analogy to example 21 using 4-chloro-3-cyclopropyl-1H-pyrazole-5-carboxylic acid (CAS: 1291275-83-6) instead of 4-chlorobenzoic acid in step (h). MS (ESI): 375.0 ([{$^{37}$Cl}M+H]$^+$), 373.0 ([{$^{35}$Cl}M+H]$^+$).

EXAMPLE 49

4-Ethoxy-N-[4-[[(1R,4R)-5-oxa-2-azabicyclo[2.2.1]heptan-4-yl]methyl]phenyl]benzamide

The title compound was obtained in analogy to example 21 using 4-ethoxybenzoic acid (CAS: 619-86-3) instead of 4-chlorobenzoic acid in step (h).

MS (ESI): 353.0 ([M+H]$^+$).

EXAMPLE 50

2-Ethyl-N-[4-[[(1R,4R)-5-oxa-2-azabicyclo[2.2.1]heptan-4-yl]methyl]phenyl]pyrimidine-5-carboxamide

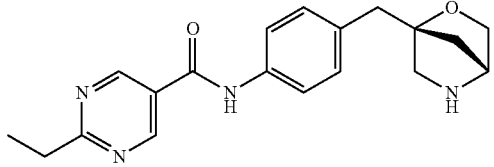 [SMILES: CCc1ncc(C(=O)Nc2ccc(C[C@@]34CN[C@@H](CO3)C4)cc2)cn1]

The title compound was obtained in analogy to example 21 using 2-ethylpyrimidine-5-carboxylic acid (CAS: 72790-16-0) instead of 4-chlorobenzoic acid in step (h).

MS (ESI): 339.0 ([M+H]$^+$).

EXAMPLE 51

2-Cyclopropyl-N-[4-[[(1R,4R)-5-oxa-2-azabicyclo[2.2.1]heptan-4-yl]methyl]phenyl]pyrimidine-5-carboxamide

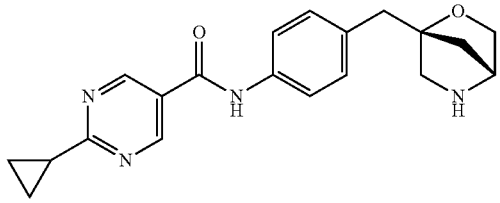 [SMILES: O=C(Nc1ccc(C[C@@]23CN[C@@H](CO2)C3)cc1)c1cnc(C2CC2)nc1]

The title compound was obtained in analogy to example 21 using 2-cyclopropylpyrimidine-5-carboxylic acid (CAS: 648423-79-4) instead of 4-chlorobenzoic acid in step (h).

MS (ESI): 351.0 ([M+H]$^+$).

EXAMPLE 52

3-Isopropyl-N-[4-[[(1R,4R)-5-oxa-2-azabicyclo[2.2.1]heptan-4-yl]methyl]phenyl]-1H-pyrazole-5-carboxamide

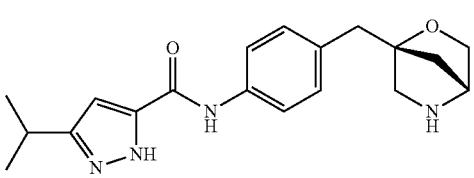 [SMILES: CC(C)c1cc(C(=O)Nc2ccc(C[C@@]34CN[C@@H](CO3)C4)cc2)[nH]n1]

The title compound was obtained in analogy to example 21 using 3-isopropylpyrazole-5-carboxylic acid (CAS: 92933-47-6) instead of 4-chlorobenzoic acid in step (h). MS (ESI): 341.3 ([M+H]$^+$).

EXAMPLE 53

4-Ethoxy-N-[4-(5-oxa-2-azabicyclo[2.2.2]octan-4-yl)phenyl]benzamide

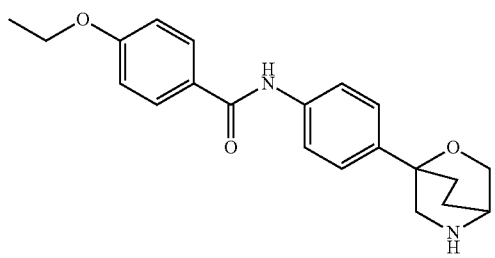 [SMILES: CCOc1ccc(C(=O)Nc2ccc(C34CCC(CO3)NC4)cc2)cc1]

The title compound was obtained in analogy to example 5 using 4-ethoxybenzamide (CAS: 55836-71-0) instead of 4-chlorobenzamide. White solid. MS (ESI): 353.2 ([M+H]$^+$).

EXAMPLE 54

4-Chloro-N-[4-[(1R,4S)-5-oxa-2-azabicyclo[2.2.1]heptan-4-yl]phenyl]benzamide

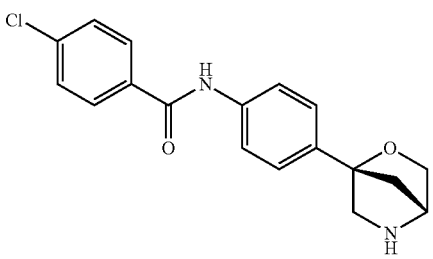 [SMILES: O=C(Nc1ccc([C@@]23CN[C@@H](CO2)C3)cc1)c1ccc(Cl)cc1]

A solution of 2,2,2-trifluoro-1-[(1R,4S)-4-(4-iodophenyl)-5-oxa-2-azabicyclo[2.2.1]heptan-2-yl]ethanone (80 mg, 0.2 mmol), 4-chlorobenzamide (37 mg, 0.24 mmol, CAS: 619-56-7), tris(dibenzylidineacetone)dipalladium(0) (36 mg, 0.04 mmol, CAS: 51364-51-3), Xantphos (38 mg, 0.08 mmol, CAS: 161265-03-8) and Cs$_2$CO$_3$ (326 mg, 1 mmol) in dioxane (2 mL) was stirred at 90° C. under N$_2$ atmosphere overnight. TLC analysis indicated complete consumption of the starting materials. The mixture was filtered. The filtrate was concentrated under reduced pressure. The residue was purified by reverse phase chromatography (C-18 column, mobile phase: A, H$_2$O; B, CH$_3$CN with 0.5% NH$_3$.H$_2$O) to give 4-chloro-N-[4-[(1R,4S)-2-(2,2,2-trifluoroacetyl)-5-oxa-2-azabicyclo[2.2.1]heptan-4-yl]phenyl]benzamide as a brown oil. 4-Chloro-N-[4-[(1R,4S)-2-(2,2,2-trifluoroacetyl)-5-oxa-2-azabicyclo[2.2.1]heptan-4-yl]phenyl]benzamide was dissolved in a mixture of MeOH (10 mL) and water (5 mL). K$_2$CO$_3$ (700 mg, 5.06 mmol) was added. The reaction mixture was stirred at room temperature for an hour. Volatiles were removed under reduced pressure. The residue was purified by prep-HPLC (C-18 column, mobile phase: A, H$_2$O; B, CH$_3$CN with 0.5% NH$_3$.H$_2$O) to give title compound (7.0 mg, 11% yield) as a white solid. MS (ESI): 331.1 ([{$^{37}$Cl}M+H]$^+$), 329.1 ([{$^{35}$Cl}M+H]$^+$).

$^1$H NMR (methanol-d$^4$, 400 MHz): δ 7.92 (d, 2H), 7.70 (d, 2H), 7.54-7.48 (m, 4H), 3.99 (m, 2H), 3.81 (s, 1H), 3.17 (m, 2H), 2.17 (d, 1H), 2.03 (d, 1H).

EXAMPLE 55

3-Chloro-N-[4-[(1R,4S)-5-oxa-2-azabicyclo[2.2.1]heptan-4-yl]phenyl]benzamide

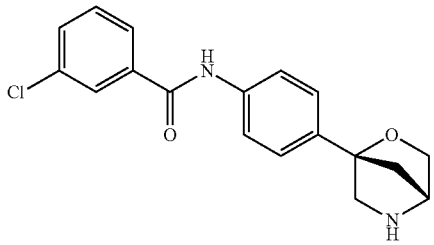 [SMILES: O=C(Nc1ccc([C@@]23CN[C@@H](CO2)C3)cc1)c1cccc(Cl)c1]

The title compound was obtained in analogy to example 54 using 3-chlorobenzamide (CAS: 618-48-4) instead of 4-chlorobenzamide. White solid.

MS (ESI): 331.1 ([{$^{37}$Cl}M+H]$^+$), 329.1 ([{$^{35}$Cl}M+H]$^+$).

EXAMPLE 56

N-[4-[(1R,4S)-5-Oxa-2-azabicyclo[2.2.1]heptan-4-yl]phenyl]-2-(trifluoromethyl)pyrimidin-4-amine

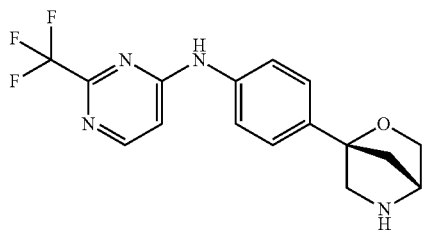 [SMILES: FC(F)(F)c1nccc(Nc2ccc([C@@]34CN[C@@H](CO3)C4)cc2)n1]

The title compound was obtained in analogy to example 20 using 2-(trifluoromethyl)pyrimidin-4-amine (CAS: 672-42-4) instead of 2-amino-5-chloropyridine in step (e). White solid. MS (ESI): 337.1 ([M+H]$^+$).

EXAMPLE 57

N-[4-[(1R,4S)-5-Oxa-2-azabicyclo[2.2.1]heptan-4-yl]phenyl]-2-(trifluoromethyl)pyridin-4-amine

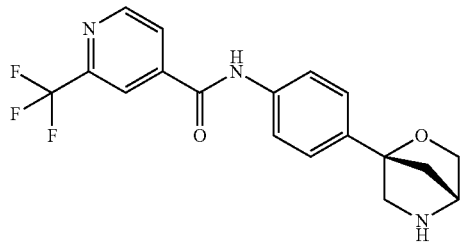 [SMILES: O=C(Nc1ccc([C@@]23CN[C@@H](CO2)C3)cc1)c1ccnc(C(F)(F)F)c1]

The title compound was obtained in analogy to example 54 using 2-(trifluoromethyl)pyridine-4-carboxamide (prepared in step [a], example 37) instead of 4-chlorobenzamide. White solid.

MS (ESI): 364.1 ([M+H]$^+$).

EXAMPLE 58

4-Chloro-N-[4-[(1S,4R)-5-oxa-2-azabicyclo[2.2.1]heptan-4-yl]phenyl]benzamide

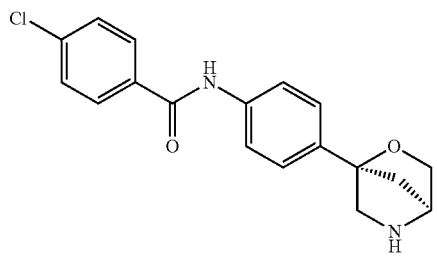 [SMILES: O=C(Nc1ccc([C@]23CN[C@H](CO2)C3)cc1)c1ccc(Cl)cc1]

a) (1S,4R)-4-Phenyl-5-oxa-2-azabicyclo[2.2.1]heptane

To a solution of tert-butyl (1S,4R)-4-phenyl-5-oxa-2-azabicyclo[2.2.1]heptane-2-carboxylate (10 g, 0.036 mol) in dry CH$_2$Cl$_2$ (100 mL) was added TFA (24.8 g, 0.22 mol) at 0° C. The reaction mixture was stirred at room temperature for 2 hours. Volatiles were removed under reduced pressure directly. The residue was purified by flash chromatography (silica gel, CH$_2$Cl$_2$: MeOH=50:1 to 5:1 by vol) to give (1S,4R)-4-phenyl-5-oxa-2-azabicyclo[2.2.1]heptane (2.1 g, 33% yield) as a yellow oil. MS (ESI): 298.2 ([M+Na$^+$]), 176.1 ([M-C$_4$H$_8$—CO$_2$+H]$^+$).

b) 2,2,2-Trifluoro-1-[(1S,4R)-4-phenyl-5-oxa-2-azabicyclo[2.2.1]heptan-2-yl]ethanone To a solution of (1S,4R)-4-phenyl-5-oxa-2-azabicyclo[2.2.1]heptane (4 g, 0.022 mol) in CH$_2$Cl$_2$ (80 mL) were added trifluoroacetic anhydride (9.2 g, 0.044 mol, CAS: 407-25-0) and Et$_3$N (6.7 g, 0.066 mol). The reaction mixture was stirred at 25° C. for 4 hours. Volatiles were removed under reduced pressure. The residue was purified by prep-HPLC (C-18 column, mobile phase: A, H₂O; B, CH₃CN with 0.5% NH₃.H₂O) to afford 2,2,2-trifluoro-1-[(1S,4R)-4-phenyl-5-oxa-2-azabicyclo[2.2.1]heptan-2-yl]ethanone (2 g, 34% yield) as a yellow oil.

MS (ESI):272.2 ([M+H]⁺).

c) 2,2,2-Trifluoro-1-[(1S,4R)-4-(4-iodophenyl)-5-oxa-2-azabicyclo[2.2.1]heptan-2-yl]ethanone To a solution of 2,2,2-trifluoro-1-[(1S,4R)-4-phenyl-5-oxa-2-azabicyclo[2.2.1]heptan-2-yl]ethanone (500 mg, 1.84 mmol) in CCl₄ (10 mL) were added [bis(trifluoroacetoxy)iodobenzene (870 mg, 2.02 mmol, CAS: 2712-78-9) and iodine (467 mg, 1.84 mmol, CAS: 7553-56-2). The reaction mixture was stirred at room temperature for 4 hours. LCMS indicated completion of the reaction. The mixture was diluted with chloroform (100 mL), washed with 5% aqueous NaHSO₃ solution (100 mL×2) and subsequently with 10% aqueous NaCl solution (100 mL). The solution was dried over Na₂SO₄. Volatiles were removed under reduced pressure. The residue was purified by flash chromatography (silica gel, petroleum ether:ethyl acetate=50:1 to 5:1 by vol) to give 2,2,2-trifluoro-1-[(1S,4R)-4-(4-iodophenyl)-5-oxa-2-azabicyclo[2.2.1]heptan-2-yl]ethanone (400 mg, 55% yield) as a yellow solid.

MS (ESI): 398.0 ([M+H]⁺).

d) 4-Chloro-N-[4-[(1S,4R)-5-oxa-2-azabicyclo[2.2.1]heptan-4-yl]phenyl]benzamide

To an oven-dried Schlenk tube were added 2,2,2-trifluoro-1-[(1S,4R)-4-(4-iodophenyl)-5-oxa-2-azabicyclo[2.2.1]heptan-2-yl]ethanone (80 mg, 0.20 mmol), 4-chlorobenzamide (38 mg, 0.24 mmol, CAS: 619-56-7), Xantphos (46 mg, 0.08 mmol, CAS: 161265-03-8), and tris(dibenzylidineacetone)dipalladium(0) (73 mg, 0.08 mmol, CAS: 51364-51-3) and Cs₂CO₃ (130 mg, 0.4 mmol). 1,4-Dioxane (3 mL) was added. The reaction mixture was stirred at 90° C. under N₂ atmosphere for 24 hours. Water (20 mL) was added. The mixture was extracted with ethyl acetate (50 mL). The organic layer was dried over Na₂SO₄. Volatiles were removed under reduced pressure. The residue was purified by prep-HPLC (C-18 column, mobile phase: A, H₂O; B, CH₃CN with 0.5% NH₃.H₂O) to afford 4-chloro-N-[4-[(1S,4R)-2-(2,2,2-trifluoroacetyl)-5-oxa-2-azabicyclo[2.2.1]heptan-4-yl]phenyl]benzamide (25 mg, 29% yield) as a yellow oil. 4-Chloro-N-[4-[(1S,4R)-2-(2,2,2-trifluoroacetyl)-5-oxa-2-azabicyclo[2.2.1]heptan-4-yl]phenyl]benzamide (25 mg, 0.065 mmol) was then dissolved in a mixture of MeOH (5 mL) and water (2 mL). K₂CO₃ (350 mg, 2.53 mmol) was added at 0° C. The reaction mixture was stirred at room temperature for an hour until LCMS analysis indicated completion of the reaction. Volatiles were removed under reduced pressure. The residue was purified by prep-HPLC (C-18 column, mobile phase: A, H₂O; B, CH₃CN with 0.5% NH₃.H₂O) to give 4-chloro-N-[4-[(1S,4R)-5-oxa-2-azabicyclo[2.2.1]heptan-4-yl]phenyl]benzamide (5 mg, 33% yield) as a white solid. MS (ESI): 331.1 ([{³⁷Cl}M+H]⁺), 329.1 ([{³⁵Cl}M+H]⁺).

¹H NMR (400 MHz, Methanol-d⁴): δ 7.95 (d, 2H), 7.72 (d, 2H), 7.56-7.50 (m, 4H), 4.01 (m, 2H), 3.83 (s, 1H), 3.19 (d, 2H), 2.19 (d, 1H), 2.04 (d, 2H).

EXAMPLE 59

3-Chloro-N-[4-[(1S,4R)-5-oxa-2-azabicyclo[2.2.1]heptan-4-yl]phenyl]benzamide

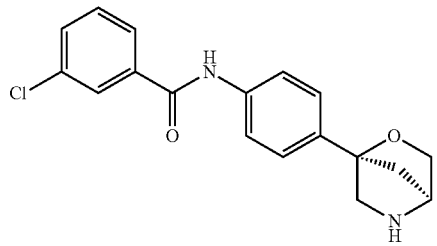 [SMILES: O=C(Nc1ccc([C@]23CN[C@H](CO2)C3)cc1)c1cccc(Cl)c1]

The title compound was obtained in analogy to example 58 using 3-chlorobenzamide (CAS: 618-48-4) instead of 4-chlorobenzamide. White solid.

MS (ESI): 331.1 ([{³⁷Cl}M+H]⁺), 329.1 ([{³⁵Cl}M+H]⁺).

EXAMPLE 60

N-[4-[(1S,4R)-5-Oxa-2-azabicyclo[2.2.1]heptan-4-yl]phenyl]-2-(trifluoromethyl)pyridine-4-carboxamide

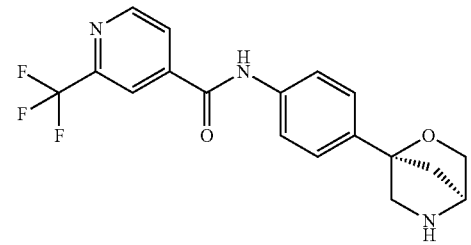 [SMILES: O=C(Nc1ccc([C@]23CN[C@H](CO2)C3)cc1)c1ccnc(C(F)(F)F)c1]

The title compound was obtained in analogy to example 58 using 2-(trifluoromethyl)pyridine-4-carboxamide (prepared in step [a], example 37) instead of 4-chlorobenzamide. White solid.

MS (ESI): 364.0 ([M+H]⁺).

EXAMPLE 61

N-[4-[(1S,4R)-5-Oxa-2-azabicyclo[2.2.1]heptan-4-yl]phenyl]-5-(trifluoromethyl)pyridin-2-amine

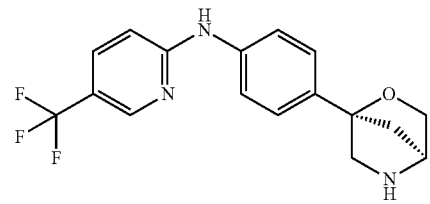 [SMILES: FC(F)(F)c1ccc(Nc2ccc([C@]34CN[C@H](CO3)C4)cc2)nc1]

To an oven-dried schlenk tube were added 2,2,2-trifluoro-1-[(1S,4R)-4-(4-iodophenyl)-5-oxa-2-azabicyclo[2.2.1]heptan-2-yl]ethanone (80 mg, 0.20 mmol), 5-(trifluoromethyl)-

2-pyridinamine (39 mg, 0.24 mmol, CAS: 74784-70-6), Xantphos (46 mg, 0.08 mmol, CAS: 161265-03-8), tris (dibenzylidineacetone)dipalladium(0) (73 mg, 0.08 mmol, CAS: 51364-51-3) and Cs$_2$CO$_3$ (130 mg, 0.4 mmol). 1,4-Dioxane (3 mL) was added. The reaction mixture was stirred at 90° C. under N$_2$ atmosphere for 24 hours. Water (20 mL) was added. The mixture was extracted with ethyl acetate (50 mL). The organic layer was dried over Na$_2$SO$_4$. Volatiles were removed under reduced pressure. The residue was purified by prep-HPLC (C-18 column, mobile phase: A, H$_2$O; B, CH$_3$CN with 0.5% NH$_3$.H$_2$O) to give 2,2,2-trifluoro-1-[(1S,4R)-4-[4-[[5-(trifluoromethyl)-2-pyridyl] amino]phenyl]-5-oxa-2-azabicyclo[2.2.1]heptan-2-yl]ethanone (35 mg, 41% yield) as yellow oil.

2,2,2-Trifluoro-1-[(1S,4R)-4-[4-[[5-(trifluoromethyl)-2-pyridyl]amino]phenyl]-5-oxa-2-azabicyclo[2.2.1]heptan-2-yl]ethanone (35 mg, 0.08 mmol) was then dissolved in a mixture of MeOH (10 mL) and water (5 mL). K$_2$CO$_3$ (500 mg, 3.61 mmol) was added at 0° C. The reaction mixture was stirred at room temperature for an hour. Volatiles were removed under reduced pressure. The residue was purified by prep-HPLC (C-18 column, mobile phase: A, H$_2$O; B, CH$_3$CN with 0.5% NH$_3$.H$_2$O) to give N-[4-[(1S,4R)-5-oxa-2-azabicyclo[2.2.1]heptan-4-yl]phenyl]-5-(trifluoromethyl) pyridin-2-amine (8 mg, 30% yield) as a white solid. MS (ESI): 336.2 ([M+H]$^+$).

$^1$H NMR (400 MHz, Methanol-d$^4$): δ 8.41 (s, 1H), 7.74 (m, 1H), 7.65 (d, 2H), 7.45 (d, 2H), 6.90 (d, 1H), 4.01 (m, 2H), 3.82 (s, 1H), 3.19 (m, 2H), 2.17 (d, 1H), 2.05 (d, 1H).

EXAMPLE 62

N-[4-[(1S,4R)-5-Oxa-2-azabicyclo[2.2.1]heptan-4-yl]phenyl]-2-(trifluoromethyl)pyrimidin-4-amine

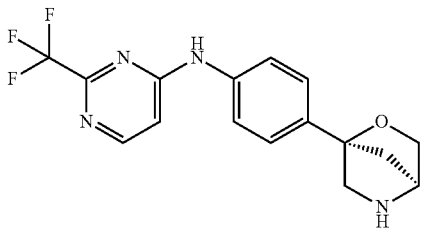 [SMILES: FC(F)(F)c1nccc(Nc2ccc([C@]34CN[C@H](CO3)C4)cc2)n1]

The title compound was obtained in analogy to example 61 using 2-(trifluoromethyl)pyrimidin-4-amine (CAS: 672-42-4) instead of 5-(trifluoromethyl)-2-pyridinamine. White solid.
MS (ESI): 337.0 ([M+H]$^+$).

EXAMPLE 63

N-[4-[[(1R,4R)-5-Oxa-2-azabicyclo[2.2.1]heptan-4-yl]methyl]phenyl]-5-(trifluoromethyl)pyridin-2-amine

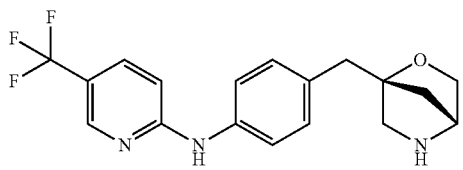 [SMILES: FC(F)(F)c1ccc(Nc2ccc(C[C@@]34CN[C@@H](CO3)C4)cc2)nc1]

The title compound was obtained in analogy to example 42 using 2-bromo-5-(trifluoromethyl)pyridine (CAS: 50488-42-1) instead of 2-bromo-5-chloropyridine. White solid. MS (ESI): 350.1 ([M+H]$^+$).

EXAMPLE 64

(RS)-amino-5-chloropyridine in step (e). White solid. MS(ESI): 351.0 ([M+H]$^+$).

EXAMPLE 65

(RS)—N-[4-(5-Oxa-2-azachloropyridine in step (e). White solid. MS(ESI): 351.0 ([M+H]$^+$).

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

EXAMPLE 66

(RS)-1-(4-Chlorophenyl)-3-[4-(5-oxa-2-azabicyclo [2.2.2]octan-4-yl)phenyl]urea

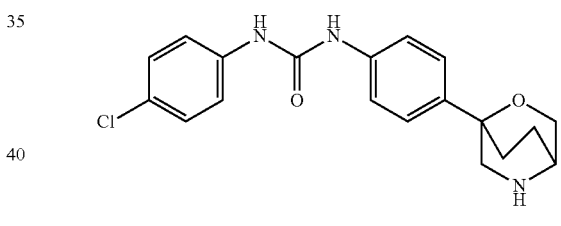

tert-Butyl 4-(4-aminophenyl)-5-oxa-2-azabicyclo[2.2.2] octane-2-carboxylate (40 mg, 0.13 mmol), 4-chlorophenyl isocyanate (22 mg, 0.14 mmol, CAS: 104-12-1) and triethylamine (64 mg, 0.5 mmol, CAS: 121-44-8) were dissolved in CH$_2$Cl$_2$ (1 mL). The solution was stirred at room temperature until LCMS analysis indicated complete consumption of the starting materials. Water (10 mL) was added. The mixture was extracted with ethyl acetate (2×20 mL). The combined organic layers were dried over Na$_2$SO$_4$, concentrated under reduced pressure, and dried under high vacuum. The residue was then dissolved in CH$_2$Cl$_2$ (2 mL). TFA (1 mL) was added to the solution. The mixture was stirred at room temperature for an hour. Volatiles were removed under reduced pressure. The residue was purified by prep-HPLC (mobile phase A: H$_2$O, B: CH$_3$CN with 0.1% TFA, C-18 column) to give (RS)-1-(4-Chlorophenyl)-3-[4-(5-oxa-2-azabicyclo[2.2.2]octan-4-yl)phenyl]urea (12 mg) as a white solid.

MS (ESI): 360.0 ([{$^{37}$Cl}M+H]$^+$), 358.0 ([{$^{35}$Cl}M+H]$^+$).

$^1$H NMR (400 MHz, Methanol-d$^4$): 7.46 (m, 4H), 7.28 (m, 4H), 4.40 (d, 1H), 4.24 (m, 1H), 3.74 (s, 1H), 3.64 (m, 1H), 3.47 (m, 1H), 2.40-2.21 (m, 4H).

EXAMPLE 67

(RS)-1-[4-(5-Oxa-2-azabicyclo[2.2.2]octan-4-yl)phenyl]-3-[4-(trifluoromethyl)phenyl]urea

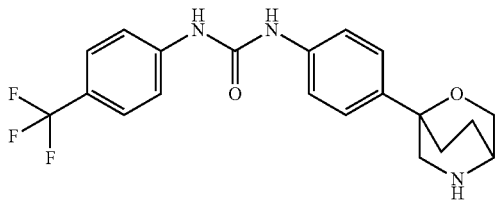 [SMILES: O=C(Nc1ccc(C(F)(F)F)cc1)Nc1ccc(C23CCC(CO2)NC3)cc1]

The title compound was obtained in analogy to example 66 using 4-(trifluoromethyl)phenyl isocyanate (CAS: 1548-13-6) instead of 4-chlorophenyl isocyanate. White solid. MS(ESI): 392.1 ([M+H]$^+$).

EXAMPLE 68

(RS)-1-(3-Chlorophenyl)-3-[4-(5-oxa-2-azabicyclo[2.2.2]octan-4-yl)phenyl]urea

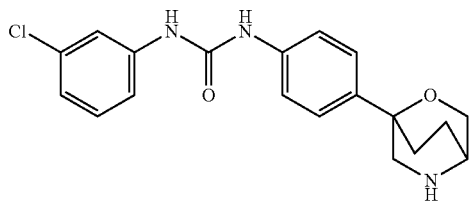 [SMILES: O=C(Nc1ccc(C23CCC(CO2)NC3)cc1)Nc1cccc(Cl)c1]

The title compound was obtained in analogy to example 66 using 3-chlorophenyl isocyanate (CAS: 2909-38-8) instead of 4-chlorophenyl isocyanate. White solid. MS (ESI): 360.0 ([{$^{37}$Cl}M+H]$^+$), 358.0 ([{$^{35}$Cl}M+H]$^+$).

MATERIALS AND METHODS

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Radioligand Binding Assay on Rat TAAR1
Membrane Preparation and Radioligand Binding.

HEK-293 cells stably expressing rat TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (K$_d$) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated K$_d$ value, that was usually around 2.3 nM, resulting in the binding of approximately 0.2% of the radioligand and a specific binding representing approximately 85% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 µM to 10 µM) in duplicates. The test compounds (20 □µl/well) were transferred into a 96 deep well plate (TrefflLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×K$_d$ in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated $K_d$ value, that was usually around 0.7 nM, resulting in the binding of approximately 0.5% of the radioligand and a specific binding representing approximately 70% of the total binding. Nonspecific binding was defined as the amount of $^3$[H]-(S)-4-[(ethyl-phenyl-amino)-methyl]-4,5-dihydro-oxazol-2-ylamine bound in the presence of 10 μM unlabeled ligand. All compounds were tested at a broad range of concentrations (10 μM to 10 μM) in duplicates. The test compounds (20 μl/well) were transferred into a 96 deep well plate (TreffLab), and 180 μl of HEPES-NaOH (20 mM, pH 7.4) containing MgCl$_2$ (10 mM) and CaCl$_2$ (2 mM) (binding buffer), 300 μl of the radioligand $^3$[H]-(S)-4-[(ethyl-phenyl-amino)-methyl]-4,5-dihydro-oxazol-2-ylamine at a concentration of 3.3×$K_d$ in nM and 500 μl of the membranes (resuspended at 60 protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 μl of Microscint 40 (PerkinElmer) the Unifilter-96 plate was sealed and after 1 hr the ratioactivity counted using a TopCount Microplate Scintillation Counter (Packard Instrument Company).

The compounds show a $K_i$ value (μM) in mouse or rat on TAAR1 (in μM) as shown in the table below.

| Example | Ki (μM) mouse/rat |
|---|---|
| 1 | 1.8153/01148 |
| 2 | 1.3461/0.0822 |
| 3 | 0.0141/2.4568 |
| 4 | 0.0111/0.3281 |
| 5 | 0.0028/0.6619 |
| 6 | 0.0044/0.7967 |
| 7 | 0.0414/0.3087 |
| 8 | 0.8464/0.0442 |
| 9 | 1.632/0.5297 |
| 10 | 0.3645/0.0209 |
| 11 | 0.019/1.2189 |
| 12 | 0.0219/7.0624 |
| 13 | 0.0304/0.624 |
| 14 | 0.136/>10 |
| 15 | 0.0853/0.0505 |
| 16 | 0.4758/0.2769 |
| 17 | 0.1118/0.2291 |
| 18 | 0.2376/0.3538 |
| 19 | 0.3344/0.063 |
| 20 | 0.0062/1.7758 |
| 21 | 0.003/0.0626 |
| 22 | 0.0126/0.0237 |
| 23 | 0.0137/0.0375 |
| 24 | 0.0086/0.0614 |
| 25 | 0.1685/0.0175 |
| 26 | 1.1384/0.441 |
| 27 | 0.0552/0.013 |
| 28 | 0.3601/1.5757 |
| 29 | 0.476/0.633 |
| 30 | 2.5493/0.6206 |
| 31 | 0.9456/0.1625 |
| 32 | >10/0.8538 |
| 33 | 5.8016/0.8806 |
| 34 | 0.0135/0.0973 |
| 35 | 0.1531/10 |
| 36 | 0.0471/1.9744 |
| 37 | 0.0377/1.4374 |
| 38 | 10.0537/0.4407 |
| 39 | 0.0022/0.0551 |
| 40 | 0.0522/0.0987 |
| 41 | 0.0183/0.066 |
| 42 | 0.0158/0.3546 |
| 43 | 0.0124/0.2022 |
| 44 | 0.0046/0.0108 |
| 45 | 0.0061/0.0212 |
| 46 | 0.0142/0.4481 |
| 47 | 0.0104/0.0104 |
| 48 | 0.0147/0.1123 |
| 49 | 0.0067/0.1423 |
| 50 | 0.2256/1.2446 |
| 51 | 0.0774/0.3237 |
| 52 | 0.295/1.1641 |
| 53 | 0.0156/1.9805 |
| 54 | 0.0054/0.9696 |
| 55 | 0.0036/0.9642 |
| 56 | 0.0393/2.4073 |
| 57 | 0.0593/1.9135 |
| 58 | 0.016/0.071 |
| 59 | 0.0054/0.0774 |
| 60 | 0.0512/0.2726 |
| 61 | 0.0146/0.0293 |
| 62 | 0.1436/0.2331 |
| 63 | 0.0107/0.1407 |
| 64 | 0.03/7.6758 |
| 65 | 0.1223/3.8384 |
| 66 | 0.005/0.0465 |
| 67 | 0.0137/0.0263 |
| 68 | 0.0119/0.0681 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Macrocrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

We claim:
1. A compound of formula

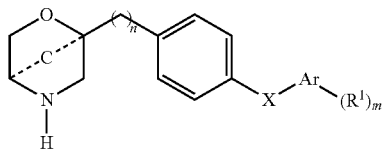

wherein
- - - - C - - - - - is —CH$_2$— or —CH$_2$—CH$_2$—;
X is —NH—, —C(O)NH— or —NHC(O)NH—;
Ar is phenyl or a 5 or 6-membered heteroaryl group containing one or two N atoms;

R$^1$ is halogen, lower alkyl, lower alkyl substituted by halogen, lower alkoxy, lower alkoxy substituted by cycloalkyl, lower alkoxy substituted by halogen or cycloalkyl;
-( )- is —CH$_2$—;
n is 0 or 1;
m is 0, 1 or 2;
or a pharmaceutically suitable acid addition salt thereof, an enantiomer, a racemic mixture, a mixture of enantiomers or an optical isomers thereof.

2. The compound of formula I according to claim 1, wherein C is —CH$_2$— and n is 1.

3. The compound of formula I according to claim 2, wherein the compound is selected from the group consisting of:
1-(4-Chlorophenyl)-3-[4-[[(1S,4S)-5-oxa-2-azabicyclo[2.2.1]heptan-4-yl]methyl]phenyl]urea;
1-(3-Chlorophenyl)-3-[4-[[(1S,4S)-5-oxa-2-azabicyclo[2.2.1]heptan-4-yl]methyl]phenyl]urea;
1-[4-[[(1S,4S)-5-Oxa-2-azabicyclo[2.2.1]heptan-4-yl]methyl]phenyl]-3-[4-(trifluoromethyl)phenyl]urea
1-(2-Chlorophenyl)-3-[4-[[(1S,4S)-5-oxa-2-azabicyclo[2.2.1]heptan-4-yl]methyl]phenyl]urea
1-[4-[[(1S,4S)-5-Oxa-2-azabicyclo[2.2.1]heptan-4-yl]methyl]phenyl]-3-[3-(trifluoromethyl)phenyl]urea
4-Chloro-N-[4-[[(1S,4S)-5-oxa-2-azabicyclo[2.2.1]heptan-4-yl]methyl]phenyl]benzamide;
4-Chloro-N-[4-[[(1S,4S)-5-oxa-2-azabicyclo[2.2.1]heptan-4-yl]methyl]phenyl]-3-propyl-1H-pyrazole-5-carboxamide;
3-Chloro-N-[4-[[(1S,4S)-5-oxa-2-azabicyclo[2.2.1]heptan-4-yl]methyl]phenyl]benzamide;
N-[4-[[(1S,4S)-5-Oxa-2-azabicyclo[2.2.1]heptan-4-yl]methyl]phenyl]-2-(trifluoromethyl)pyridine-4-carboxamide;
4-Ethoxy-N-[4-[[(1S,4S)-5-oxa-2-azabicyclo[2.2.1]heptan-4-yl]methyl]phenyl]benzamide;
1-[4-[[(1R,4R)-5-Oxa-2-azabicyclo[2.2.1]heptan-4-yl]methyl]phenyl]-3-[4-(trifluoromethyl)phenyl]urea;
1-(4-Chlorophenyl)-3-[4-[[(1R,4R)-5-oxa-2-azabicyclo[2.2.1]heptan-4-yl]methyl]phenyl]urea;
1-(3-Chlorophenyl)-3-[4-[[(1R,4R)-5-oxa-2-azabicyclo[2.2.1]heptan-4-yl]methyl]phenyl]urea;
4-(Cyclopropylmethoxy)-N-[4-[[(1S,4S)-5-oxa-2-azabicyclo[2.2.1]heptan-4-yl]methyl]phenyl]benzamide;
6-Ethoxy-N-[4-[[(1S,4S)-5-oxa-2-azabicyclo[2.2.1]heptan-4-yl]methyl]phenyl]pyridine-3-carboxamide;
N-[4-[[(1S,4S)-5-Oxa-2-azabicyclo[2.2.1]heptan-4-yl]methyl]phenyl]-6-(2,2,2-trifluoroethoxy)pyridine-3-carboxamide;
2-Cyclopropyl-N-[4-[[(1S,4S)-5-oxa-2-azabicyclo[2.2.1]heptan-4-yl]methyl]phenyl]pyrimidine-5-carboxamide;
4-Chloro-3-cyclopropyl-N-[4-[[(1S,4S)-5-oxa-2-azabicyclo[2.2.1]heptan-4-yl]methyl]phenyl]-1H-pyrazole-5-carboxamide;
5-Chloro-N-[4-[[(1S,4S)-5-oxa-2-azabicyclo[2.2.1]heptan-4-yl]methyl]phenyl]pyridin-2-amine
N-[4-[[(1S,4S)-5-Oxa-2-azabicyclo[2.2.1]heptan-4-yl]methyl]phenyl]-5-(trifluoromethyl)pyridin-2-amine;
N-[4-[[(1S,4S)-5-Oxa-2-azabicyclo[2.2.1]heptan-4-yl]methyl]phenyl]-5-(trifluoromethyl)pyrazin-2-amine;
N-[4-[[(1S,4S)-5-Oxa-2-azabicyclo[2.2.1]heptan-4-yl]methyl]phenyl]-5-(trifluoromethyl)pyrimidin-2-amine;
3-Isopropyl-N-[4-[[(1S,4S)-5-oxa-2-azabicyclo[2.2.1]heptan-4-yl]methyl]phenyl]-1H-pyrazole-5-carboxamide;

3-Chloro-N-[4-[[(1R,4R)-5-oxa-2-azabicyclo[2.2.1]heptan-4-yl]methyl]phenyl]benzamide;
N-[4-[[(1R,4R)-5-Oxa-2-azabicyclo[2.2.1]heptan-4-yl]methyl]phenyl]-2-(trifluoromethyl)pyridine-4-carboxamide;
4-Chloro-N-[4-[[(1R,4R)-5-oxa-2-azabicyclo[2.2.1]heptan-4-yl]methyl]phenyl]-3-propyl-1H-pyrazole-5-carboxamide;
5-Chloro-N-[4-[[(1R,4R)-5-oxa-2-azabicyclo[2.2.1]heptan-4-yl]methyl]phenyl]pyridin-2-amine;
1-(2-Chlorophenyl)-3-[4-[[(1R,4R)-5-oxa-2-azabicyclo[2.2.1]heptan-4-yl]methyl]phenyl]urea;
1-[4-[[(1R,4R)-5-Oxa-2-azabicyclo[2.2.1]heptan-4-yl]methyl]phenyl]-3-[3-(trifluoromethyl)phenyl]urea;
4-(Cyclopropylmethoxy)-N-[4-[[(1R,4R)-5-oxa-2-azabicyclo[2.2.1]heptan-4-yl]methyl]phenyl]benzamide;
6-Ethoxy-N-[4-[[(1R,4R)-5-oxa-2-azabicyclo[2.2.1]heptan-4-yl]methyl]phenyl]pyridine-3-carboxamide;
N-[4-[[(1R,4R)-5-Oxa-2-azabicyclo[2.2.1]heptan-4-yl]methyl]phenyl]-6-(2,2,2-trifluoroethoxy)pyridine-3-carboxamide;
4-Chloro-3-cyclopropyl-N-[4-[[(1R,4R)-5-oxa-2-azabicyclo[2.2.1]heptan-4-yl]methyl]phenyl]-1H-pyrazole-5-carboxamide;
4-Ethoxy-N-[4-[[(1R,4R)-5-oxa-2-azabicyclo[2.2.1]heptan-4-yl]methyl]phenyl]benzamide;
2-Ethyl-N-[4-[[(1R,4R)-5-oxa-2-azabicyclo[2.2.1]heptan-4-yl]methyl]phenyl]pyrimidine-5-carboxamide;
2-Cyclopropyl-N-[4-[[(1R,4R)-5-oxa-2-azabicyclo[2.2.1]heptan-4-yl]methyl]phenyl]pyrimidine-5-carboxamide;
3-Isopropyl-N-[4-[[(1R,4R)-5-oxa-2-azabicyclo[2.2.1]heptan-4-yl]methyl]phenyl]-1H-pyrazole-5-carboxamide; and
N-[4-[[(1R,4R)-5-Oxa-2-azabicyclo[2.2.1]heptan-4-yl]methyl]phenyl]-5-(trifluoromethyl)pyridin-2-amine; or,
a pharmaceutically acceptable salt thereof.

4. The compound of formula I according to claim 1, wherein ———C——— is —CH$_2$— and n is 0.

5. The compound of formula I according to claim 4, wherein the compound the compound is selected from the group consisting of:
5-Chloro-N-[4-[(1S,4R)-5-oxa-2-azabicyclo[2.2.1]heptan-4-yl]phenyl]pyridin-2-amine;
5-Chloro-N-[4-[(1R,4S)-5-oxa-2-azabicyclo[2.2.1]heptan-4-yl]phenyl]pyridin-2-amine;
4-Chloro-N-[4-[(1R,4S)-5-oxa-2-azabicyclo[2.2.1]heptan-4-yl]phenyl]benzamide;
3-Chloro-N-[4-[(1R,4S)-5-oxa-2-azabicyclo[2.2.1]heptan-4-yl]phenyl]benzamide;
N-[4-[(1R,4S)-5-Oxa-2-azabicyclo[2.2.1]heptan-4-yl]phenyl]-2-(trifluoromethyl)pyrimidin-4-amine;
N-[4-[(1R,4S)-5-Oxa-2-azabicyclo[2.2.1]heptan-4-yl]phenyl]-2-(trifluoromethyl)pyridin-4-amine;
4-Chloro-N-[4-[(1S,4R)-5-oxa-2-azabicyclo[2.2.1]heptan-4-yl]phenyl]benzamide;
3-Chloro-N-[4-[(1S,4R)-5-oxa-2-azabicyclo[2.2.1]heptan-4-yl]phenyl]benzamide;
N-[4-[(1S,4R)-5-Oxa-2-azabicyclo[2.2.1]heptan-4-yl]phenyl]-2-(trifluoromethyl)pyridine-4-carboxamide;
N-[4-[(1S,4R)-5-Oxa-2-azabicyclo[2.2.1]heptan-4-yl]phenyl]-5-(trifluoromethyl)pyridin-2-amine; and,
N-[4-[(1S,4R)-5-Oxa-2-azabicyclo[2.2.1]heptan-4-yl]phenyl]-2-(trifluoromethyl)pyrimidin-4-amine; or,
a pharmaceutically acceptable salt thereof.

6. The compound of formula I according to claim 1, wherein ———C——— is —CH$_2$CH$_2$— and n is 1.

7. The compound of formula I according to claim 1, wherein ———C——— is —CH$_2$CH$_2$— and n is 0.

8. The compound of formula I according to claim 7, wherein the compound is selected from the group consisting of:
(RS)-5-Chloro-N-[4-(5-oxa-2-azabicyclo[2.2.2]octan-4-yl)phenyl]pyridin-2-amine;
(RS)—N-[4-(5-Oxa-2-azabicyclo[2.2.2]octan-4-yl)phenyl]-5-(trifluoromethyl)pyridin-2-amine;
(RS)-4-Chloro-N-[4-(5-oxa-2-azabicyclo[2.2.2]octan-4-yl)phenyl]benzamide;
3-Chloro-N-[4-(5-oxa-2-azabicyclo[2.2.2]octan-4-yl)phenyl]benzamide;
(RS)-4-(Cyclopropylmethoxy)-N-[4-(5-oxa-2-azabicyclo[2.2.2]octan-4-yl)phenyl]benzamide;
(RS)-6-Ethoxy-N-[4-(5-oxa-2-azabicyclo[2.2.2]octan-4-yl)phenyl]pyridine-3-carboxamide;
(RS)—N-[4-(5-Oxa-2-azabicyclo[2.2.2]octan-4-yl)phenyl]-6-(2,2,2-trifluoroethoxy)pyridine-3-carboxamide;
(RS)-2-Cyclopropyl-N-[4-(5-oxa-2-azabicyclo[2.2.2]octan-4-yl)phenyl]pyrimidine-5-carboxamide;
(RS)-4-Chloro-N-[4-(5-oxa-2-azabicyclo[2.2.2]octan-4-yl)phenyl]-3-propyl-1H-pyrazole-5-carboxamide;
(RS)-2-Ethyl-N-[4-(5-oxa-2-azabicyclo[2.2.2]octan-4-yl)phenyl]pyrimidine-5-carboxamide;
N-[4-(5-Oxa-2-azabicyclo[2.2.2]octan-4-yl)phenyl]-2-(trifluoromethyl)pyrimidin-4-amine;
(RS)—N-[4-(5-Oxa-2-azabicyclo[2.2.2]octan-4-yl)phenyl]-2-(trifluoromethyl)pyridine-4-carboxamide;
4-Ethoxy-N-[4-(5-oxa-2-azabicyclo[2.2.2]octan-4-yl)phenyl]benzamide;
(RS)—N-[4-(5-Oxa-2-azabicyclo[2.2.2]octan-4-yl)phenyl]-5-(trifluoromethyl)pyrazin-2-amine;
(RS)—N-[4-(5-Oxa-2-azabicyclo[2.2.2]octan-4-yl)phenyl]-5-(trifluoromethyl)pyrimidin-2-amine;
(RS)-1-(4-Chlorophenyl)-3-[4-(5-oxa-2-azabicyclo[2.2.2]octan-4-yl)phenyl]urea;
(RS)-1-[4-(5-Oxa-2-azabicyclo[2.2.2]octan-4-yl)phenyl]-3-[4-(trifluoromethyl)phenyl]urea; and,
(RS)-1-(3-Chlorophenyl)-3-[4-(5-oxa-2-azabicyclo[2.2.2]octan-4-yl)phenyl]urea; or,
a pharmaceutically acceptable salt thereof.

9. A process for the manufacture of a compound of formula according to claim 1, which process comprises cleaving off the N-protecting group (R$^2$) from compounds of formula 9-1 to afford a

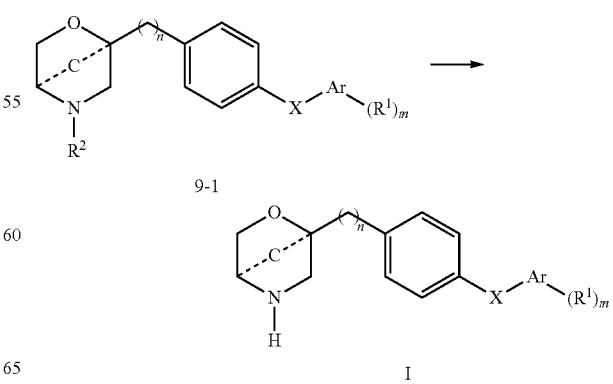

compound of formula I wherein $R^2$ is a N-protecting group selected from —C(O)O-tert-butyl or —C(O)CF$_3$, and, optionally converting I into a pharmaceutically acceptable acid addition salt.

10. A pharmaceutical composition comprising a compound of claim 1 and at least on pharmaceutically acceptable excipient, carrier or adjuvant.

11. A method for treating depression, anxiety disorders, bipolar disorder, attention deficit hyperactivity disorder (ADHD), stress-related disorders, psychotic disorders, schizophrenia, neurological diseases, Parkinson's disease, neurodegenerative disorders, epilepsy, migraine, hypertension, substance abuse, metabolic disorders, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders comprising administering to a patient in need thereof a therapeutically effective amount of a compound according to claim 1.

\* \* \* \* \*